(12) United States Patent
Mukherjee et al.

(10) Patent No.: US 9,029,557 B2
(45) Date of Patent: *May 12, 2015

(54) LABELED A4B2 LIGANDS AND METHODS THEREFOR

(71) Applicant: The Regents of the University of California, Oakland, CA (US)

(72) Inventors: Jogeshwar Mukherjee, Irvine, CA (US); Sharon A. Kuruvilla, San Jose, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/760,703

(22) Filed: Feb. 6, 2013

(65) Prior Publication Data

US 2014/0050663 A1     Feb. 20, 2014

Related U.S. Application Data

(63) Continuation-in-part of application No. 11/721,145, filed as application No. PCT/US2005/045538 on Dec. 1, 2005, now Pat. No. 8,378,109.

(60) Provisional application No. 60/634,368, filed on Dec. 7, 2004.

(51) Int. Cl.
  *C07D 401/12* (2006.01)
  *A61K 51/04* (2006.01)

(52) U.S. Cl.
  CPC ............ *C07D 401/12* (2013.01); *A61K 51/044* (2013.01); *A61K 51/0455* (2013.01)

(58) Field of Classification Search
  CPC ..................................................... C07D 401/12
  USPC ........................................... 546/276.4, 279.1
  See application file for complete search history.

(56) References Cited

U.S. PATENT DOCUMENTS

| 5,278,176 | A | 1/1994 | Lin et al. |
| 5,629,325 | A | 5/1997 | Lin et al. |
| 5,691,365 | A | 11/1997 | Crooks et al. |
| 5,733,912 | A | 3/1998 | Wasicak et al. |
| 5,914,328 | A | 6/1999 | Lin et al. |
| 5,948,793 | A | 9/1999 | Abreo et al. |
| 8,378,109 | B2 * | 2/2013 | Mukherjee et al. ........ 546/276.4 |
| 2004/0132737 | A1 | 7/2004 | Cormier et al. |
| 2005/0119309 | A1 | 6/2005 | Papke et al. |
| 2005/0130990 | A1 | 6/2005 | Cormier et al. |

FOREIGN PATENT DOCUMENTS

| EP | 1185521 | 10/2004 |
| WO | 99/32480 | 7/1999 |
| WO | 0182978 | 11/2001 |
| WO | 02057275 | 7/2002 |
| WO | 02076434 | 10/2002 |
| WO | 03070731 | 8/2003 |
| WO | 2004069144 | 8/2004 |
| WO | 2005000250 | 1/2005 |
| WO | 2005000806 | 1/2005 |
| WO | 2005011612 | 2/2005 |
| WO | 2005032479 | 4/2005 |

OTHER PUBLICATIONS

Sihver, Wiebke et al., Development of ligands for in vivo imaging of cerebral nicotinic receptors, Behavioral Brain Research, Feb. 2000, pp. 143-157, Elsevier Science B.V., Sweden.

Lin, N-H et al., "Structure-Activity Sutdies on 2-Methyl-3-(2(S)-pyrrolidinylmethoxy)pyridine (ABT-089): An Orally Bioavailable 3-Pyridyl Ether Nicotinic Acetylcholine Receptor Ligand with Cognition-Enhancing Properties", Journal of Medical Chemistry, 1997, vol. 40, pp. 385-390.

Lin, N-H et al., "Synthesis and Structure-Activity Relationships of Pyridine-Modified Analogs of 3-[2-((S)-Pyrrolidinyl)Methoxy]Pyridine, A-84543, A Potent Nicotinic Acetylcholine Receptor Agonist", Bioorganic and Medicinal Chemistry Letters, 1998, vol. 8, pp. 249-254.

Rueter, L.E. et al., "ABT-089: Pharmacological Properties of a Neuronal Nicotinic Acetylcholine Receptor Agonist for the Potential Treatment of Cognitive Disorders", CNS Drug Review, 2004, vol. 10, No. 2, pp. 167-182.

* cited by examiner

*Primary Examiner* — Patricia L Morris
(74) *Attorney, Agent, or Firm* — Fish & Tsang LLP

(57) ABSTRACT

Contemplated compositions and methods are employed to bind in vitro and in vivo to an α4β2 nicotinic acetylcholine receptor in a highly selective manner. Where such compounds are labeled, compositions and methods employing such compounds can be used for PET and SPECT analysis. Alternatively, and/or additionally contemplated compounds can be used as antagonists, partial agonists or agonists in the treatment of diseases or conditions associated with α4β2 dysfunction.

12 Claims, 10 Drawing Sheets

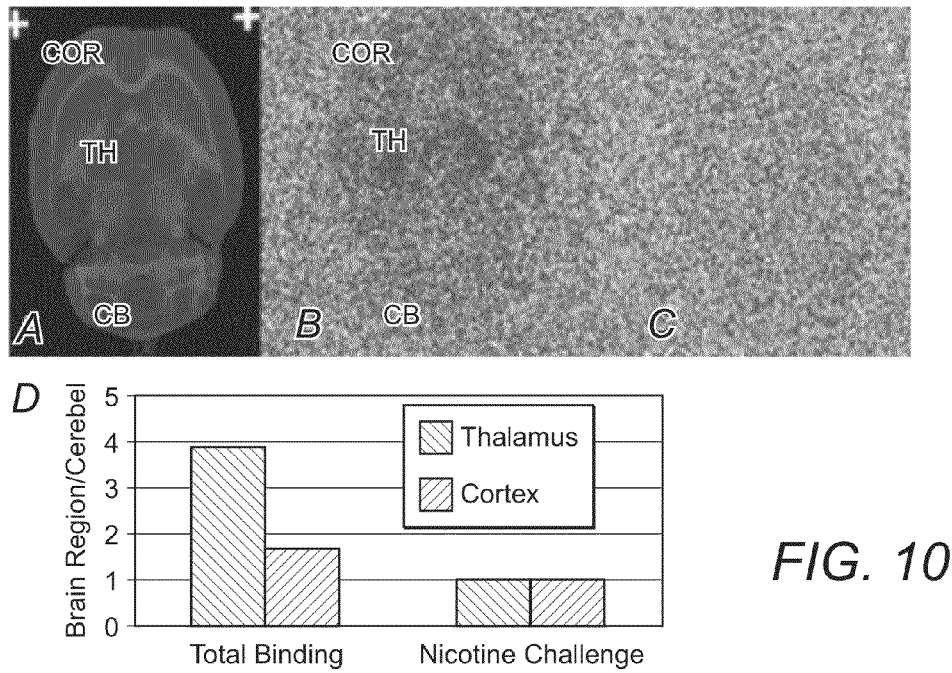
FIG. 10
FIG. 11
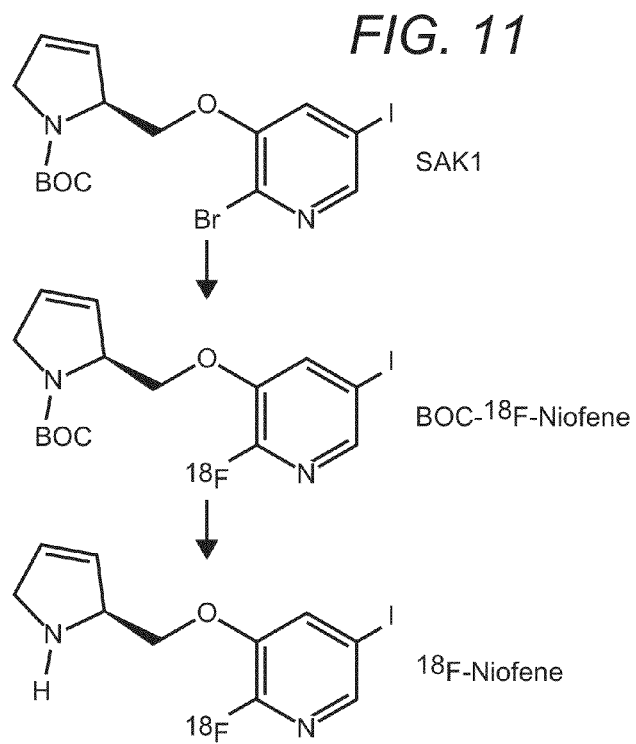

LABELED A4B2 LIGANDS AND METHODS THEREFOR

This application is a continuation-in-part application of US application with the Ser. No. 11/721,145, now U.S. Pat. No. 8,378,109, which was filed Jul. 21, 2009 as a national phase application of PCT/US05/45538, which was filed Dec. 1, 2005, which claims priority to our U.S. provisional patent application with the Ser. No. 60/634,368, which was filed Dec. 7, 2004, all of which are incorporated by reference herein.

This invention was made with government support from the National Institutes of Health (NIH/NIA) Grant number R01 AG 029479. The government may have certain rights in the invention.

BACKGROUND OF THE INVENTION

Nicotinic acetylcholine receptors (nAChRs) belong to the superfamily of ligand-gated ion channels and are distributed widely in the human and nonhuman brain. At least 17 different subunits are currently known, which can coassemble in several ways resulting in 3 distinct types of nAChRs: (a) heteromeric receptors found in neuromuscular junctions, (b) heteromeric receptors found in the neurons, and (c) homomeric receptors also found in the neurons. These receptors mediate some effects of the endogenous neurotransmitter acetylcholine (ACh) and are also the biologic target of the tobacco alkaloid nicotine, which is known to mimic the actions of ACh at these receptors. Subunit compositions determine functional properties such as ion selectivity, conductance, channel open times, rate of desensitization, and sensitivity to certain neurotoxins.

Several nAChRs have been identified and characterized pharmacologically and have distinct patterns of distribution in the brain. For example, the nicotine α4β2 receptor subtypes are thought to play a role in various diseases, including various brain disorders (e.g., Alzheimer's disease), behavioral disorders (e.g., schizophrenia or substance abuse), various neoplasms (e.g., lung cancer), and other diseases (see e.g., J. Neurobiol. 2002; 53:633-640). It has been suggested that the loss of the α4β2 receptors may be an early presymptomatic marker for Alzheimer's disease (Prog Neurobiol. 2000; 61:75-111). These neuronal receptors may also be involved in the addiction to nicotine in chronic tobacco users, and tobacco use may increase the number of the α4β2 receptor sites (Annu Rev Pharmacol Toxicol. 1996; 36:597-613).

Therefore, and not surprisingly, the development of non-invasive imaging methods using PET and SPECT of the α4β2 receptor system has gained significant interest. For example, in previously known methods, PET studies have been performed with 11C-nicotine. However, the moderate affinity of nicotine for the α4β2 receptors resulted in relatively rapid clearance, and thus precluded its usefulness as a radiotracer. Based on the discovery of epibatidine binding to the α4β2 receptor (see e.g., Mol. Pharmacol. 1994; 45:563-569), various PET and SPECT radioligands have been developed (e.g., Behav Brain Res. 2000; 113:143-157), including various epibatidine analogs (e.g., WO 2005/000806) and pyridylether analogs that have been radiolabeled with 11C, 18F, 76Br, or 123I. Structures of these ligands are depicted in FIG. 1. Still other radioligands have been prepared in an effort to optimize in vivo imaging properties (see e.g., Bioorg Med. Chem. 2001; 9:3055-3058; J Nucl Med. 2004; 45:878-884; Bioorg Med. Chem. 2003; 11:5333-5343). However, toxicity issues and undesirable kinetic parameters have slowed the progression of these radiotracers for human studies. Nonetheless, human SPECT studies have now begun with 5-$^{123}$I-A85380, and PET studies have begun with 2-$^{18}$F-A85380 and, more recently, with 6-$^{18}$F-A85380 (for structures, see FIG. 1).

Still further known α4β2 nAChR ligands include those described in EP 1 185 521, WO 2002/076434, and WO 2002/57275, with agonist activity, and various plant derived compounds (e.g., tetrahydroberberine, tetrahydropalmatine, stepholidine) with agonist and antagonist activity were described in WO 2004/069144. Other known agonist compounds include metanicotine compounds and azaadamantane-type compounds as presented in WO 2001/082978, and various substituted hexahydro-1H-pyrrolizines as discussed in U.S. Pat. No. 5,733,912.

It should be noted that almost all of the PET and SPECT radioligands developed thus far for the α4β2 nAChR subtype have been agonists, and only few selected α4β2 ligands with antagonistic activity were described in U.S. Pat. No. 5,691,365. Other known antagonists include lophotoxin, neosurugatoxin, and erysodine (J. Med. Chem. (1997) 40: 4169-4194). It has been suggested that α4β2 nAChRs may occur in 4 possible conformations: (a) a resting state, when no agonist is present; (b) an activated state, when an agonist is present and the ion channel is open; (c) a transiently desensitized state, when the ion channel is closed for small lengths of time (i.e., seconds); and (d) a desensitized state, when the ion channel is closed for longer periods of time. ACh is known to bind with different affinities to these different states (e.g., ACh has higher affinity for desensitized states). Remarkably, there are no published data that would indicate whether antagonists also would have different affinities for the various states, and/or whether their in vivo binding pattern would be different compared with that of the agonists such as 2-$^{18}$F-A85380. Only recently, a derivative was prepared that included a $^{18}$F-radiolabel attached to the N-pyrrolidine ring ([$^{18}$F]3-[1-(3-fluoropropyl)-(S)-pyrrolidin-2-ylmethoxy]-pyridine in: J. Label Compd Radiopharm. 2003; 46:1261-1268). While that compound revealed good in vitro affinity for the α4β2 receptor, no specific data were provided on the differential active states in the nicotinic ACh receptor. Moreover, in vivo studies failed to provide conclusive images or data that would co-localize the PET signals with known locations for the α4β2 receptor.

Therefore, while there are numerous radioligands for receptors of the α4β2 receptor type known in the art, all or almost all of them suffer from one or more disadvantages. Consequently, there is still a need to provide improved compositions and methods for radioligands for receptors of the α4β2 receptor type. Viewed from another perspective, there is also a need for selective positron emission tomography (PET) and single photon emission computed tomography (SPECT) radiotracers for animal and human diagnostic imaging studies.

SUMMARY OF THE INVENTION

The present invention is directed to compositions and methods for targeting the α4β2 receptor, wherein compounds in such compositions will selectively bind to the α4β2 receptor and (in most instances) evoke an antagonistic effect. Where the compounds are labeled, it is contemplated that binding and/or location of the α4β2 receptor may be analyzed in vitro and in vivo.

In one aspect of the inventive subject matter, contemplated compounds will have a structure according to Formula I

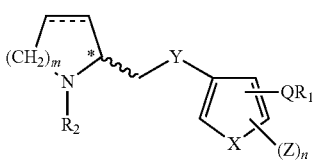

Formula I in which X is CH=CH, CH=N, N=CH, O, S, or NR₃, where R₃ is H or optionally substituted lower alkyl; Y is O, S, or NR₃; ---- is an optional double bond; Q is optionally substituted lower alkyl; R₁ is selected from the group consisting of H, halogen, halogen isotope, leaving group, trialkyltin, and trialkylamine; or Q and R₁ taken together are null where ---- is a double bond and where n is 1 or 2; Z is independently halogen, halogen isotope, NO₂, or trialkylamine; m and n are independently 0 to 3, inclusive; and R₂ is selected from the group consisting of hydrogen, optionally substituted lower alkyl, and a nitrogen protecting group.

Especially preferred compounds further include those in which X is N=CN, Y is O, R₂ is hydrogen or alkyl, Q is propyl, m is 1 and n is 0, and wherein R₁ is fluoride or radiolabeled fluoride (and in which ---- is a double bond), or in which X is N=CN, Y is O, R₂ is hydrogen or alkyl, Q and R₁ taken together are null, wherein ---- is a double bond, and wherein n is 1 or 2. Thus, among other preferred compounds, preferred compounds include various optionally substituted 3-(pyrrolidin-2-ylmethoxy)-pyridines, optionally substituted 3-(2,5-dihydro-1H-pyrrol-2-ylmethoxy)-pyridines, optionally substituted 3-(azetidin-2-ylmethoxy)-pyridines, wherein some of the substituents may include a halogen (optionally radioisotope).

In a further aspect of the inventive subject matter, contemplated compounds will have a structure according to Formula X

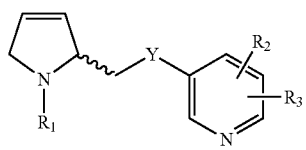

Formula X in which R₁ is hydrogen, a lower alkyl, or a nitrogen protecting group, Y is O, S, or NR₁, and R₂ and R₃ are independently a leaving group, a halogen, or a halogen isotope. Still further preferred compounds include those in which R₂ and R₃ are independently a halogen or a halogen isotope, or in which R₂ and R₃ are both a halogen or both a halogen isotope, or in which wherein R₂ and R₃ are a halogen and a halogen isotope, respectively. Additionally, it is contemplated that the compounds according to Formula X may also include those in which R₂ is I and wherein R₃ is F, or wherein R₂ is ¹²³I and wherein R₃ is F, or wherein R₂ is I and wherein R₃ is ¹⁸F, or in which R₂ and R₃ are both a leaving group.

In another aspect, a pharmaceutical composition includes at least one of contemplated compounds (preferably in oral or parenteral formulation) at a concentration effective to treat a disease associated with α4β2 receptor dysfunction. In preferred aspects of such compositions, the concentration is effective to provide an antagonist effect at the α4β2 receptor, while the disease is a cognitive dysfunction, anxiety disorder, neurodegenerative disease, schizophrenia, pain, depression, epilepsy, Tourette's syndrome, small-cell lung to carcinoma, or tobacco dependence.

Further contemplated aspects include methods of diagnosing a mammal having a disease associated with an α4β2 receptor dysfunction in which contemplated compounds are administered to the mammal (typically in a labeled form) at a dosage effective to locate and/or quantify in vivo binding of the labeled compound to the α4β2 receptor. Preferably, the label is a halogen isotope suitable for detecting the compound in vivo using PET or SPECT, and contemplated compounds are parenterally administered.

Various objects, features, aspects and advantages of the present invention will become more apparent from the following detailed description of preferred embodiments of the invention.

BRIEF DESCRIPTION OF THE DRAWING

FIG. 10 shows rat brain autoradiography of $^{123}$I-niodene. A. Rat brain slice showing cortex (COR), thalamus (TH) and cerebellum (CB); B. Same brain slice showing binding of $^{123}$I-niodene; C. Displacement of $^{123}$I-niodene in the presence of 300 μM nicotine; D. Ratio of $^{123}$I-niodene binding in thalamus and cortex versus cerebellum.

FIG. 11 shows radiolabeling of the brominated precursor (SAKI) with fluorine-18 in order to prepare $^{18}$F-Niofene. The synthesis involves two steps, one is the incorporation of fluorine-18 and second is the deprotection of the nitrogen to result in $^{18}$F-Niofene as a new potential PET and SPECT (when labeled with $^{123}$I) imaging agent.

DETAILED DESCRIPTION

Figure 1:
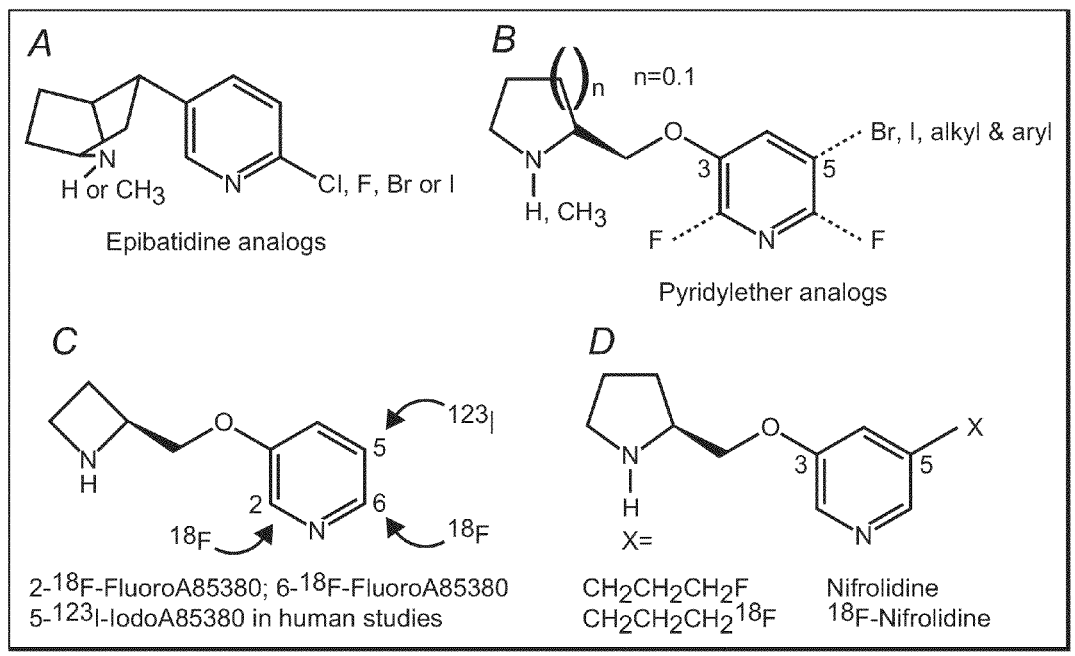
FIG. 1 depicts chemical structures of various known α4β2 radioligands in which (A) denotes epibatidine analogs, (B) denotes pyridylether analogs, (C) denotes azetidinylether analogs, and (D) denotes exemplary structures of compounds contemplated herein.

The inventors have discovered that radiolabeled α4β2 receptor antagonists can be prepared that provide specific interaction with α4β2 receptor type receptors in both in vitro and in vivo environments. More specifically, contemplated compounds preferably include an halogen and/or (halo)alkyl substituted pyridine, wherein the substituted pyridine is further coupled to a (dehydro)pyrrolidine or azetidine via an ether, thioether, or amino group.

Particularly preferred compounds therefore include 5-(3'-$^{18}$F-fluoropropyl)-3-(2-(S)-pyrrolidinylmethoxy)pyridine, 5-(3'-$^{18}$F-fluoropropyl)-3-(2-(S)-3,4-dehydropyrrolidinylmethoxy)pyridine, 2-($^{18}$F)-3-(2-(S)-pyrrolidinylmethoxy)pyridine, 2-($^{18}$F)-3-(2-(S)-3,4-dehydropyrrolidinylmethoxy)pyridine, 3-(Azetidin-2-ylmethoxy)-5-(3-$^{18}$F propyl)-pyridine, and 3-(Azetidin-2-ylmethoxy)-2-($^{18}$F-pyridine, wherein the $^{18}$F may also be replaced by $^{19}$F or other halogen (optionally isotope). Such compounds are especially useful is targeting the α4β2 receptor system for diagnostic and/or therapeutic applications. Remarkably, most of contemplated compounds are antagonists, or expected to be antagonists for the α4β2 receptor. Such antagonistic action appears to be supported by the finding that inclusion of alkyl groups at the 5-position in the pyridine ring of certain pyridyl ethers leads to a change from an agonist to an antagonist character.

Still further particularly preferred compounds include 2-Fluoro-5-iodo-3-[2-(S)-3,4-dehydropyrrolinylmethoxy] pyridine (Niofene), or 2-$^{18}$F-5-iodo-3-[2-(S)-3,4-dehydropyrrolinylmethoxy]pyridine ($^{18}$F-Niofene), or 2-Fluoro-5-$^{123}$I-iodo-3-[2-(S)-3,4-dehydropyrrolinylmethoxy]pyridine ($^{123}$I-Niofene), and precursors thereof. Niofene contains both a fluorine atom and an iodine atom and can therefore advantageously be used for PET studies when labeled with fluorine-18 and for SPECT studies when labeled with iodine-123. Such compounds are especially desirable as these nicotine receptor imaging agents selectively bind to the α4β2 receptors (e.g., in the brain). Moreover, these compounds also clear out from the rest of the brain in a rapid manner. Therefore, using such compounds, one can measure quantitatively the distribution of the α4β2 receptors in the brain and possibly other parts of the body, which is considered to have significant diagnostic utility for various diseases (e.g., Alzheimer's disease, Schizophrenia, some aspects of oncology, and/or predisposition to substance abuse).

It should still further be particularly appreciated that contemplated compounds (and especially those according to Formulae X-XIV) will provide significant advantages, including (a) The ligands are antagonists and are expected to have significantly lower toxicity, (b) precursor compounds for radiolabeling purposes can be prepared for fluorine-18 or iodine-123 incorporation, (c) compounds show selectivity for α4β2 receptors in the brain, (d) Fluorine-18 and iodine-123 compounds are stable in vivo in animals, and (e) the radiolabeled compounds are suitable for PET and SPECT imaging.

Based on these and other considerations, the inventor particularly contemplated use of a haloalkyl, and especially a 3'-fluoropropyl group at the 5-position in the pyridylether linked to a pyrrolidine ring. In such compounds, it was hypothesized that the fluorine at a 3-position will only have a minimal effect on the pyridine nitrogen. Furthermore, radiolabeling at that position affords substantial distance from the pyrrolidine nitrogen. While other substituents were also contemplated, the pyrrolidine ring is especially preferred as such compounds were expected to provide a moderate-affinity compound for the α4β2 receptor. On the other hand, where a compound with higher affinity is desired, an azetidine ring system may be employed in place of the pyrrolidine ring, which is expected to exhibit higher affinity to the α4β2 receptor. In yet further particularly preferred aspects, the pyrrolidine ring may also be desaturated to form a dehydropyrrolidine ring, which has demonstrated significantly faster binding kinetics (due to rapid reversible binding), which will result in faster PET and/or SPECT analyses.

Contemplated Compounds

Compounds presented herein are contemplated to be useful for diagnosis and/or treatment of various diseases associated with the α4β2 receptor, as well as research and development of new drugs and/or drug-receptor interactions. Therefore, it is generally preferred that the compounds according to the inventive subject matter have a structure that (a) binds to the α4β2 receptor, (b) has an antagonistic effect, and/or (c) is detectable in vitro and in vivo using detection methods (most preferably based on radiation) well known in the art. Most preferably, detection of the compound in vivo and/or in vitro collocates with the location of the α4β2 receptor.

In one aspect of the inventive subject matter, contemplated compounds will have a structure according to Formulae I, wherein the compounds may have one or more asymmetric centers or groups that may give rise to isomeric, tautomeric, or other steric isoforms (e.g., R—, and/or S-configuration, E/Z configuration, tautomeric isoforms, enantiomers, diastereomers, etc.), and wherein each of such forms and mixtures thereof are expressly contemplated herein.

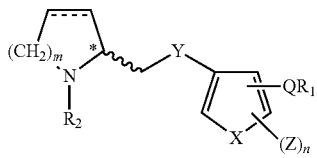

Formula I in which X is CH═CH, CH═N—, —N═CH, O, S or NR3, where R3 is selected from H, C1-C4 alkyl, aryl, or aralkyl; Y is O, S or NR3; Q is C1-C6 saturated or unsaturated, chiral or achiral, straight or branched, cyclic or acyclic, optionally substituted hydrocarbon radical; $R_1$ is a halogen (and most preferably a fluoride, or radiolabeled fluoride ($^{18}$F)), trialkyltin, trialkylamine, a leaving group (and most preferably bromide, iodide, mesylate, tosylate, triflate, nosylate, or brosylate), or Q and R1 taken together are null where ⸺ is a double bond and where n is 1 or 2; Z is a halogen (most preferably fluoride, or radiolabeled fluoride ($^{18}$F)); ⸺ is an optional double bond; m and n are independently 0 to 3, inclusive; $R_2$ is H or C1-C6 saturated or unsaturated, chiral or achiral, straight or branched, cyclic or acyclic, optionally substituted hydrocarbon group, or is a nitrogen protecting group (e.g., tertbutoxycarbonyl, acetate, trifluoroacetate, trityl, etc.).

Most preferably, contemplated compounds have a structure according to Formulae II, III, IV, V, VI, VII, VIII, and IX, with radicals as defined above, and in which $R_1'$ and $R_1''$ are independently as defined in $R_1$.

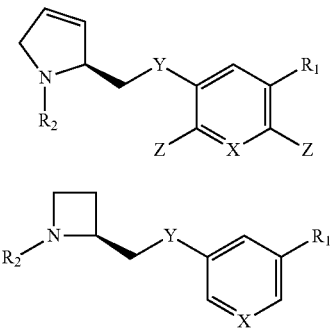

Formula II

Formula III

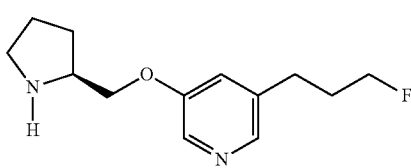

Formula IV

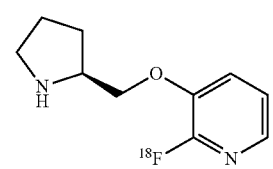

Formula V

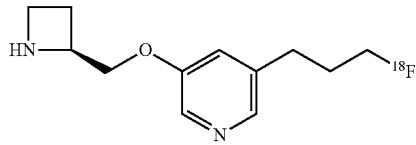

Formula VI

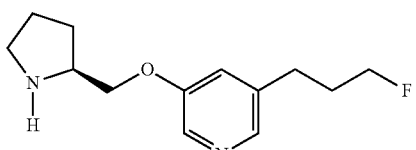

Formula VII

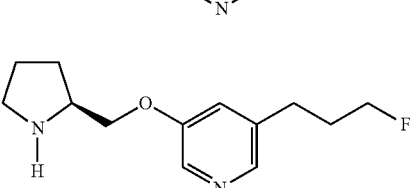

Formula VIII

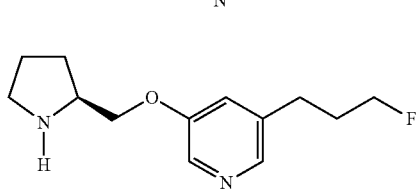

Formula IX

In addition, still further contemplated compounds will include those according to Formula X Formula X in which $R_1$ is hydrogen, a lower alkyl, or a nitrogen protecting group (e.g., carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, acetyl (Ac) group, benzoyl (Bz) group, benzyl (Bn) group, carbamate group, p-Methoxybenzyl (PMB) group, 3,4-Dimethoxybenzyl (DMPM) group, p-methoxyphenyl (PMP) group, Tosyl (Ts) group and further sulfonamide (Nosyl & Nps) groups, etc.), Y is O, S, or NR$_1$, and R$_2$ and R$_3$ are independently a leaving group, a halogen, or a halogen isotope. Depending on the particular use, R$_2$ and R$_3$ can independently be a halogen or a halogen isotope, or both the same (i.e., both are a halogen or a halogen isotope, typically distinct halogen). For example, R$_2$ can be I and while R$_3$ is F, or R$_2$ can be $^{123}$I and R$_3$ is F, or R$_2$ can be I and R$_3$ is $^{18}$F. As should be appreciated, the (radiolabeled) halogen can be introduced via replacement of a suitable leaving group. Thus, R$_2$ and R$_3$ are also independently contemplated to be a leaving group (e.g., diazonium salts, oxonium ions, nonaflates, triflates, fluorosulfonates, tosylates, mesylates, halogens, nitrates, phosphates, and other inorganic esters, tetraalkylammonium salts, esters, and acid anhydrides when attached to carbonyl carbon, ammonium salts, phenoxides, alcohols, and carboxylic acids when attached to carbonyl carbon, ethers, and esters when attached to carbonyl carbon).

Therefore, and among other choices, especially preferred compounds will have a structure according to Formulae XI-XIV Formula XI

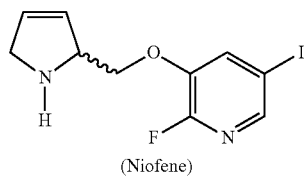

(Niofene)

Formula XII

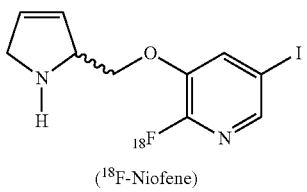

($^{18}$F-Niofene)

Formula XIII

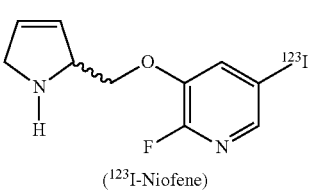

($^{123}$I-Niofene)

Formula XIV

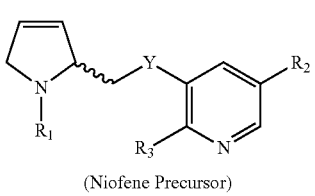

(Niofene Precursor)

Formula XV

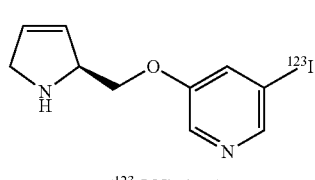

($^{123}$-I-Niodene)

in which $R_1$ is a nitrogen protecting group or hydrogen, and in which $R_2$ and $R_3$ are independently a leaving group or halogen.

Where appropriate, it should be recognized that the pyridine ring system (or other ring system as indicated in the Formulae above) may be substituted with one or more substituents. Similarly, or additionally, the optionally desaturated pyrrolidine ring of contemplated compounds may be replaced with a heterocyclic (typically N as heteroatom) ring system. Contemplated compounds may further include polar or ionic groups, and it is contemplated that such groups may be neutralized by forming the corresponding salt forms. While generally all anions and cations are deemed suitable for use herein, especially preferred salts are formed from pharmaceutically acceptable acids and bases. For example, contemplated compounds in anionic form may form a salt with $K^+$, $Na^+$, $Mg^{++}$, or $Ca^{++}$, while cationic forms may form salts with tartrate, mesylate, citrate, etc.

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.).

Similarly, the term "alkenyl" as used herein refers to an alkyl in which at least one carbon-carbon bond is a double bond. Thus, the term "lower alkenyl" includes all alkenyls with one to ten carbon atoms. The term "cycloalkenyl" as used herein refers to a cyclic or polycyclic group containing 3 to 15 carbons and at least one double bond. Likewise, the term "alkynyl" as used herein refers to an alkyl or alkenyl in which at least one carbon-carbon bond is a triple bond. Thus, the term "lower alkynyl" includes all alkynyls with one to ten carbon atoms.

As still further used herein, the term "alkoxy" refers to a —OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or substituted cycloheteroalkyl. Similarly, the term "aryloxy" refers to a —OAr group, wherein Ar is an aryl, substituted aryl, heteroaryl, or substituted heteroaryl group.

Furthermore, the terms "aryl" and "Ar" are used interchangeably herein and refer to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). Similarly, the terms "heterocycle" or "heterocyclic ring" are used interchangeably herein and refer to a saturated, partially or entirely unsaturated, or aromatic carbocyclic group having a single ring (e.g., morpholino, pyridyl or furyl) or multiple condensed rings (e.g., naphthpyridyl, quinoxalyl, quinolinyl, or indolizinyl) which include at least one heteroatom within the ring(s). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like. Thus, the term "heteroaryl" refers to a heterocycle in which at least one heterocyclic ring is aromatic.

Still further, the term "substituted" as used herein means that a hydrogen atom that is covalently bound to a group or atom (or a free electron pair or electron pair of a double bond of an atom) is replaced by a covalently bound non-hydrogen substituent, including hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

The term "prodrug" as used herein refers to a modification of contemplated compounds, wherein the modified compound exhibits less pharmacological activity (as compared to the unmodified compound) and wherein the modified compound is converted within a target cell or target organ back into the unmodified form. For example, conversion of contemplated compounds into prodrugs may be useful where the active drug is too toxic for safe systemic administration, or where the contemplated compound is poorly absorbed by the digestive tract, or where the body breaks down the contemplated compound before reaching its target.

The term "halogen" as used herein refers to any one of a fluoride, chloride, bromide, and iodide halogen radical, wherein the radical may be an isotope or a non-isotope. For example, suitable fluoride isotopes include $^{18}$F, iodide isotopes include $123^{125}$I, and $^{131}$I, and contemplated chloride isotopes include $^{36}$Cl and $^{37}$Cl.

The term "Nifrolidine" as used herein refers to 3-(3-Fluoro-propyl)-5-(pyrrolidin-2-ylmethoxy)-pyridine, the term "Nifrolene" as used herein refers to 3-(2,5-Dihydro-1H-pyrrol-2-ylmethoxy)-5-(3-fluoro-propyl)-pyridine, and the term "Nifene" refers to 3-(2,5-Dihydro-1H-pyrrol-2-ylmethoxy)-2-fluoro-pyridine, wherein the fluoride in each of these compounds may or may not be a radioisotope. The term "Niofene" as used herein refers to 2-Fluoro-5-iodo-3-[2-(S)-3,4-dehydropyrrolinylmethoxy]pyridine wherein the fluorine and/or the iodine in the compound may or may not be a radioisotope (e.g., 2-$^{18}$F-5-iodo-3-[2-(S)-3,4-dehydropyrrolinylmethoxy]pyridine, or 2-Fluoro-5-$^{123}$I-iodo-3-[2-(S)-3,4-dehydropyrrolinylmethoxy]pyridine). The term "Niodene" as used herein refers to 3-iodo-5-[2-(S)-3-pyrrolinylmethoxy]pyridine. Unless specified to the contrary, each of these compounds may be present in the R- and/or S-configuration.

It is further contemplated that compounds according to the inventive subject matter may also be prepared in a prodrug form in which such compounds are modified to improve at least one of solubility, selectivity towards neural tissue (or other tissue that expresses the α4β2 receptor), toxicity, and/or pharmacokinetic or pharmacodynamic parameter. There are numerous manner for preparation of prodrugs known in the art, and all of such known manners are contemplated herein. For example, suitable prodrug approaches are described in Prodrugs (Drugs and the Pharmaceutical Sciences: a Series of Textbooks and Monographs) by Kenneth B. Sloan (ISBN: 0824786297), or in Hydrolysis in Drug and Prodrug Metabolism: Chemistry, Biochemistry, and Enzymology by Bernard Testa (ISBN: 390639025X), which are to the appropriate extent incorporated by reference herein.

Similarly, it should be noted that contemplated compounds may also be less active in the form as described herein, and be more active as metabolite or metabolites that are formed in vivo. For example, contemplated compounds may be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc.

Contemplated Compositions

The compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion). Preferably, the compositions are administered orally, intraperitoneally, or intravenously.

For example, sterile injectable forms of contemplated compounds may be aqueous solutions or oleaginous suspensions. These suspensions may be formulated according to techniques known in the art using suitable dispersing or wetting agents and suspending agents. The sterile injectable preparation may also be prepared as a sterile injectable solution or suspension in a non-toxic parenterally acceptable diluent or solvent, for example as a solution in 1,3-butanediol. Among other acceptable vehicles and solvents, especially contemplated liquids include water, Ringer's solution, and isotonic sodium chloride solution. In addition, sterile, fixed oils may be employed as a co-solvent or suspending medium (e.g., natural or synthetic mono- or diglycerides). Fatty acids may also be used, and suitable fatty acids include oleic acid and its glyceride derivatives, olive oil, castor oil, especially in their polyoxyethylated versions. Such oil solutions or suspensions may further contain a long-chain alcohol diluent or dispersant.

In another example, contemplated compounds may be orally administered in any orally acceptable dosage form, including capsules, tablets, aqueous suspensions, or solutions. In the case of tablets for oral use, all pharmaceutically acceptable carriers (e.g., lactose, corn to starch, etc) are deemed suitable. Similarly, various lubricating agents may be added (e.g., magnesium stearate). For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The pharmaceutical compositions of this invention may also be administered topically, especially when the target of treatment includes areas or organs readily accessible by topical application, including diseases of the eye, the skin, the lower intestinal tract, or areas exposed during surgical intervention. There are numerous topical formulations known in the art, and all of such formulations are deemed suitable for use herein.

For topical applications, contemplated compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

Pharmaceutical compositions according to the inventive subject matter may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred embodiments, contemplated compounds will be present in an amount of between about 0.1 ng/ml to about 100 mg/ml, more typically in an amount of between about 10 ng/ml to about 10 mg/ml, and most typically between about 1 µg/ml to about 100 µg/ml. Where the formulation is a solid, contemplated compounds will be present in an amount of between about 0.1 ng/g to about 100 mg/g, more typically in an amount of between about 10 ng/g to about 10 mg/g, and most typically between about 1 µg/g to about 100 µg/g. With respect to a dosage unit, it is generally contemplated that contemplated compounds are administered at a dosage effective to achieve a desired therapeutic effect or at a dosage effective to provide visualization in vitro and/or in vivo.

Therefore, suitable amounts of contemplated compounds will be in the range of 0.1 μg per dosage unit to about 0.5 gram per dosage unit, more typically between 10 μg per dosage unit to about 0.05 gram per dosage unit, and most typically between 50 μg per dosage unit to about 100 mg per dosage unit. Thus, suitable dosages will be in the range of about 0.01 μg/kg and 100 mg/kg, more typically between 1 μg/kg and 50 mg/kg, and most typically between 10 μg/kg and 10 mg/kg.

It should be especially appreciated that where the compounds include radioisotopes as a labeling and/or therapeutic moiety, the amount of radiation emitted per dosage unit will generally be considered medically reasonable. Therefore, suitable radiation dosages will be between about 0.1 mGy to about 1 cGy over the course of exposure. Therefore, and especially where relatively small quantities of contemplated compounds are administered, relatively high specific activities are preferred. For example, suitable specific activities of radiolabeled compounds will be between 10 and 300 GBq/μmol, more typically between 50 and 250 GBq/μmol, and most typically between 100 and 200 GBq/μmol (corresponding to radiochemical yields of between about 20-40%).

Contemplated Uses

Contemplated compounds may be particularly useful as ligands for the α4β2 nAChR, and most preferably as an antagonist for the α4β2 nAChR. Regardless of the activity profile of contemplated compounds, it should be appreciated that due to the specific binding of the compounds presented herein ($K_m$ to α4β2 nAChR is typically at least 10-100 times less than compared to other receptors or biological structures) numerous diagnostic, therapeutic, and academic uses are contemplated.

For example, and especially where contemplated compounds are radiolabeled, it should be appreciated that such compounds may be useful for location and/or quantification of α4β2 nAChR in a biological tissue. Suitable diagnostic methods will generally depend on the particular label, and it should be appreciated that the label may be introduced in numerous manners. Among other appropriate labels, $^{18}F$, $^{11}C$, $^{123/125/131}I$ may be included into the compounds where the compound should be detected in vivo via PET or SPECT analysis. On the other hand, where the compound should be detected in vitro via autoradiography or scintigraphy, suitable labels include $^{14}C$, $^{18}F$, or $^{123/131}I$. Most preferably, the label will be a radioisotope of an atom that is already present in the compound. However, where desirable, radiolabeled groups with atoms other than those present in the compound may be added to the structured presented herein (e.g., $^{32/33}P$ via phosphate groups, or $^{35}S$ via sulfate or sulfoxide group). Location and quantification of the α4β2 receptor in vivo may be particularly useful in diagnostic use, while quantification of the receptor and/or binding of contemplated labeled compounds in vitro may be especially useful in characterization of a mutant form of a receptor, or in competitive analysis with a second ligand. Therefore, labeled compounds may also be particularly useful in the development and/or characterization of new ligands. With respect to the imaging and/or quantification method, it should be noted that all known devices and methods are deemed suitable for use herein. While not especially preferred, alternative labels include optically detectable labels, including fluorescent labels, luminescent labels, colloidal gold, and/or UV/VIS absorbing labels.

In other examples of contemplated uses, and particularly where compounds presented herein are not radioisotope-containing compounds, it should be recognized that the binding of the compounds to the α4β2 nAChR as antagonist (or in some cases as agonist) may be used in a therapeutic manner for treatment of diseases or conditions that are associated with the nAChR. For example, diseases and conditions to be treated with contemplated compounds include cognitive dysfunctions and/or attentional disorders (e.g., anxiety disorders, lack of mental focus, ADHD), neurodegenerative diseases (e.g., Alzheimer's and Parkinson's), schizophrenia, pain, depression, epilepsy, Tourette's syndrome, small-cell lung carcinoma, and tobacco dependence.

Experimental Data

Materials and Methods

All chemicals and solvents were of high grade from Aldrich Chemical Co.

Electrospray mass spectra were obtained on a model 7250 mass spectrometer (Micromass LCT). Proton nuclear magnetic resonance (NMR) spectra were acquired on a General Electric NMR Omega 500 MHz.

High-specific-activity $^{18}F$-fluoride was produced in the MC-17 cyclotron or the CTI RDS-112 cyclotron using an $^{18}O$-enriched water target ($^{18}O$ to $^{18}F$ using p,n reaction). The high-specific-activity $^{18}F$-fluoride was used in subsequent reactions. Chromatographic separations were performed on semipreparative reverse-phase columns using the Gilson high-performance liquid chromatography (HPLC) systems.

$^{18}F$ radioactivity was counted in a Capintec dose calibrator, whereas low-level counting was performed in a well counter (Cobra Quantum; Packard Instruments Co.). Radioactive thin-layer chromatographs were obtained by scanning in a Bioscan System 200 Imaging scanner (Bioscan, Inc.). Rat brain slices were obtained on a Leica 1850 cryotome. 18F autoradiographic studies were performed by exposing tissue samples on storage phosphor screens. The apposed phosphor screens were read by a Cyclone Storage Phosphor System (Packard Instruments Co.). Monkey PET studies were performed using a high-resolution ECAT EXACT HR-scanner (Siemens/CTI).

All radioiodinations were carried out by using no-carrier-added $Na^{123}I$ (MDS Nordion®, supplied in 0.1N NaOH) from Nordion Inc, Ontario, Canada.

All animal studies were approved by the Institutional Animal Care and Use Committee of University of California at Irvine and Wright State University.

Synthesis

The following synthetic scheme is provided to give exemplary guidance to a person of ordinary skill in the art to prepare and use contemplated compounds. However, while the below protocol is limited to certain of contemplated compounds, it should be understood that numerous other of the compounds presented herein may be synthesized following the guidelines given below. For example, the pyrrolidine moiety may be substituted with one or more substituents (e.g., using sulfoxy instead of methoxy group, having additional halogen or alkyl groups, etc), or may be at least partially desaturated (e.g., to form the corresponding dehydropyrrolidine group, etc. Likewise, the pyridine moiety may be provided with one or more leaving groups (typically different leaving groups) and/or a halogen to so allow introduction of a radiolabeled halogen (e.g., $R_2$ in Formula X could be a halogen, a nitro group, a quarternary ammonium group, while $R_3$ in Formula X could be a halogen, trialkyl tin, or other leaving groups). Thus, it should be recognized that numerous modifications may be made without departing from the inventive concept herein.

5-Bromo-3-Hydroxypyridine

Figure 2:
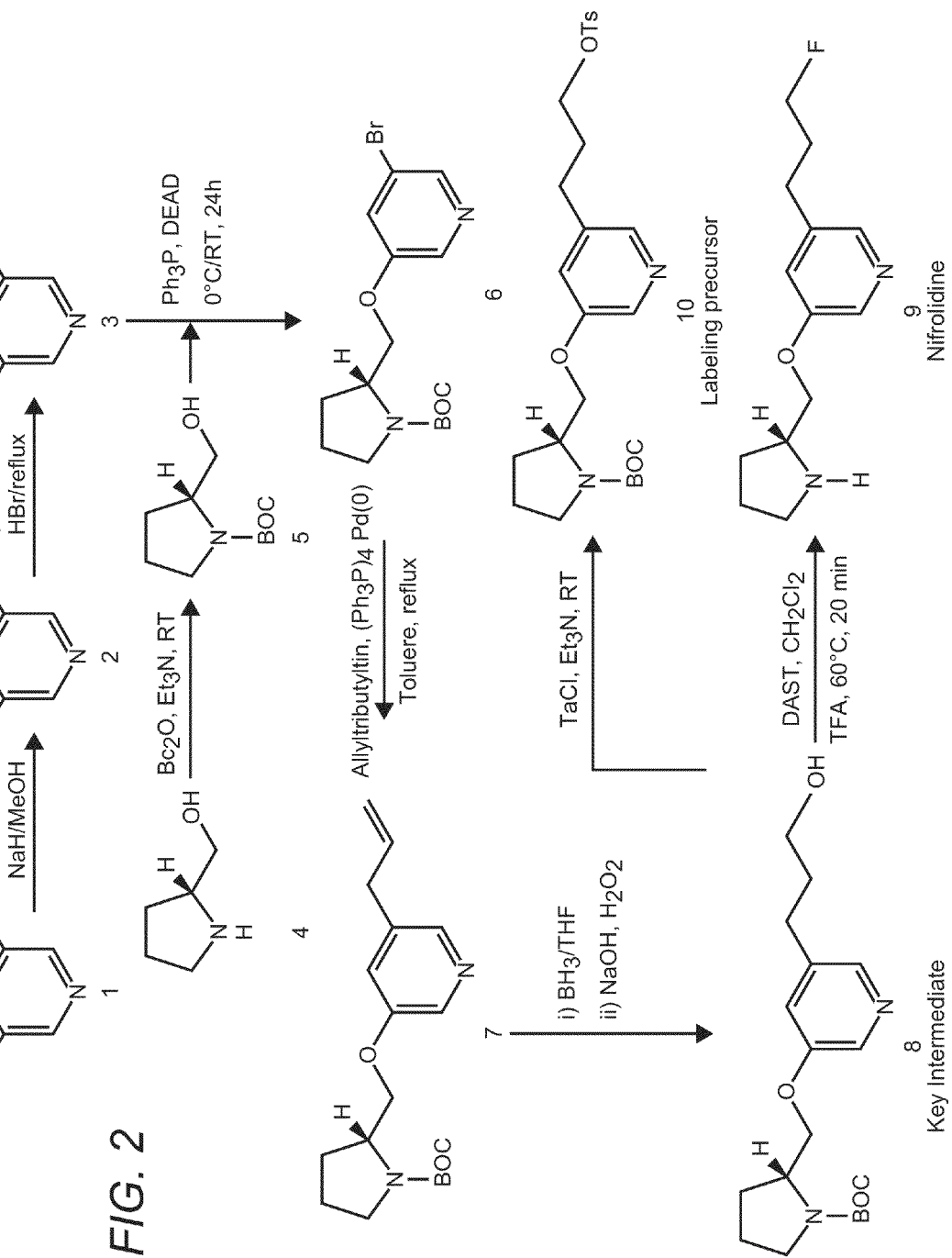
FIG. 2 depicts an exemplary synthesis scheme for 5-(3'-fluoropropyl)-3-(2-(S)-pyrrolidinylmethoxy)-pyridine (9, nifrolidine) and a corresponding tosylate precursor, 5-(3-[[4-methylphenyl]sulfonyloxy]propyl)-3-(1-BOC-2-(S)-pyrrolidinylmethoxy)pyridine (10) for radiolabeling with ¹⁸F.

Using reported procedures, 3,5-dibromopyridine 1 (5 g, 21 mmol) was dissolved in 100 mL anhydrous methanol (FIG. 2). The solution was cooled to 0° C. and 16 g of sodium hydride (60% [w/w]) mineral oil suspension) were added in portions. This mixture was stirred for 1 h at room temperature and refluxed at 80° C. for 4 h. The solvent was removed by rotary evaporation. The residue was taken in 100 mL of water. The mixture was extracted with dichloromethane (3×100 mL). The organic portions were combined, dried (anhydrous magnesium sulfate), filtered, and evaporated, and the residue (3.5 g) was characterized as 5-bromo-3-methoxypyridine 2. The 5-bromo-3-methoxypyridine 2 was refluxed with 20 mL concentrated (57%) hydrogen bromide for 24 h. The reaction was quenched with saturated NaHCO$_3$ solution, and the basic mixture was extracted with dichloromethane (3×50 mL). The organic portions were pooled together, dried (magnesium sulfate), filtered, evaporated to provide the 5-bromo-3-hydroxypyridine 3 (3 g, 82%) in >95% purity as ascertained by thin-layer chromatography (TLC) (Rf=0.5, ethyl acetate/hexane, 1:1). NMR (CDCl$_3$, 500 MHz)-ppm: 8.28 (d, 1H, J=1.8 Hz), 8.24 (d, 1H, J=2.7 Hz), 7.38 (dd, 1H, J=1.8, 2.7 Hz). MS, m/z, 173, 175 (25%, [M+H]$^+$).

5-Bromo-3-(1-BOC-2-(S)-Pyrrolidinylmethoxy) Pyridine (BOC=Butoxycarbonyl)

Di-tert-butyl dicarbonate (4.3 g, 19.7 mmol) was added to a cold (0° C.) mixture of 2-(S)-pyrrolidinemethanol 4 (2 g, 19.7 mmol) and triethylamine (2.8 mL, 20 mmol). After the mixture was stirred at room temperature for 30 min, 20 mL of dichloromethane were added and washed with saturated NaHCO3 (2×20 mL) and water (1×20 mL). The organic layer was dried (MgSO4), filtered, and concentrated to provide 1-BOC-2-(S)-pyrrolidinemethanol 5 (3.5 g, 88%) in >95% purity (MS, m/z, 224 (65%, [M+Na]$^+$). Diethyl azodicarboxylate (DEAD) (1.8 mL, 12 mmol) was added to a solution of triphenylphosphine (3.1 g, 12 mmol) in anhydrous tetrahydrofuran (THF) (30 mL) at 0° C., and the mixture was stirred for 30 min. A solution of 1-BOC-2-(S)-pyrrolidinemethanol (5) (2 g, 10 mmol) in 5 mL THF and 3-bromo-5-hydroxypyridine (3) (2 g, 11.4 mmol) in 5 mL THF was added at 0° C. The reaction mixture was allowed to stand at room temperature for 24 h. The solvent was removed by rotary evaporation and the residue was dissolved in dichloromethane (100 mL) and washed with saturated NaHCO3 (50 mL) and water (3×50 mL). The organic solution was dried over anhydrous MgSO4, filtered, and concentrated to oil. The crude oil was purified by silica column chromatography (hexane/ethyl acetate, 1:1) to afford the title compound 6 (1.56 g, 44%). NMR: (CDCl$_3$, 500 MHz)-ppm: 8.26 (dd, 2H, J=15, 1.8 Hz), 7.37 (t, 1H, J=2.4 Hz), 3.92 (dm, 2H, J=34.7 Hz), 3.54 (m, 1H), 3.01 (m, 2H), 1.93 (m, 2H), 1.79 (m, 2H), 1.65 (s, 9H). MS, m/z, 379, 381 (5%, [M+Na]$^+$).

5-Allyl-3-(1-BOC-2-(S)-Pyrrolidinylmethoxy)Pyridine

A mixture of 5-bromo-3-(1-BOC-2-(S)-pyrrolidinylmethoxy)pyridine (6) (1.56 g, 4.4 mmol), tetrakis(triphenylphosphine)palladium (0) (40 mg, 0.03 mmol), and allyltributyl tin (1.5 mL, 4.4 mmol) in toluene (50 mL) was refluxed for 24 h. The mixture was filtered and the filtrate was evaporated. The residue so obtained was chromatographed (silica, ethyl acetate/hexane, 1:1) to afford the title compound 7 (800 mg, 57%). NMR (CDCl$_3$, 500 MHz)-ppm: 8.16 (d, 1H, J=2.5 Hz), 8.06 (d, 1H, J=13.7 Hz), 7.05 (d, 1H, J=27.7), 5.92 (m, 1H), 5.11 (m, 2H), 4.15 (m, 3H), 3.37 (d, 4H), 2.02 (m, 4H), 1.47 (s, 9H). MS, m/z, 319 (25%, [M+H]$^+$), 341 (28%, [M+Na]$^+$).

5-(3-Hydroxypropyl)-3-(1-BOC-2-(S)-Pyrrolidinylmethoxy)-Pyridine

A solution of allyl derivative 7 (750 mg, 2.3 mmol) in THF (5 mL) was cooled (0° C.). To this solution was added diborane in THF (4.5 mL, 6.7 mmol), and the mixture was stirred at 0° C. for 1 h followed by 1 h at room temperature. The reaction was cooled (0° C.), and then 3N NaOH (5 mL) was added, followed by 30% aqueous hydrogen peroxide (200 µL). The reaction mixture was stirred at 0° C. for 30 min and then at room temperature for 30 min. The THF was removed by rotary evaporation, and the resulting mixture was extracted with dichloromethane (3×5 mL). The combined organic extracts were dried (MgSO4), filtered, and concentrated to afford crude sticky product that was purified by preparative TLC (PTLC), silica to provide (ethyl acetate/hexane, 1:1) pure 8 (200 mg, 26%). NMR (CDCl$_3$, 500 MHz)-ppm: 8.10 (s, 1H), 8.04 (s, 1H), 7.60 (s, 1H), 4.11 (m, 2H), 3.95 (m, 1H), 3.65 (m, 2H), 3.39 (m, 2H), 2.78 (m, 2H), 1.99 (m, 6H), 1.47 (s, 9H). MS, m/z, 337 (95%, [M+H]$^+$), 359 (45%, [M+Na]$^+$).

5-(3-Fluoropropyl)-3-(2-(S)-Pyrrolidinylmethoxy) Pyridine

The N—BOC alcohol 8 (40 mg, 0.12 mmol) in chloroform (200 µL) was treated with diethylaminosulfur trifluoride (DAST) (15.5 µL, 0.12 mmol) at 0° C. The reaction mixture was allowed to warm to room temperature and kept overnight. For work-up, 2 mL of chloroform and 2 mL of water were added to the reaction mixture, and the organic layer was separated and washed with 10% NaHCO3 (2×1 mL). The organic layer was dried (anhydrous sodium sulfate), filtered, and evaporated, and the residue was purified by PTLC (ethyl acetate/hexane, 1:1) to afford pure 5-(3-fluoropropyl)-3-(1-BOC-2-(S)-pyrrolidinylmethoxy)pyridine (10 mg, 25%). NMR (CDCl3, 500 MHz)-ppm: 8.17 (d, 1H, J=2.2 Hz), 8.08 (d, 1H, J=15 Hz), 7.08 (d, 1H, J=38.8 Hz), 4.47 (dt, 2H, J=47.2, 5.8 Hz), 4.15 (m, 2H), 3.92 (m, 1H), 3.40 (m, 2H), 2.76 (m, 2H), 2.03 (m, 6H), 1.47 (s, 9H). MS, m/z, 339 (25%, [M+H]$^+$), 361 (100%, [M+Na]$^+$). Deprotection of the N—BOC fluorinated derivative was performed by treatment with trifluoroacetic acid (TFA). The 5-(3-fluoropropyl)-3-(1-BOC-2-(S)-pyrrolidinylmethoxy)-pyridine (7 mg, 0.02 mmol) was dissolved in 0.8 mL dichloromethane and 0.2 mL TFA. The solution was heated at 80° C. for 30 min. Solvents were removed in vacuo and the residue was neutralized to pH 9 with saturated sodium carbonate. The aqueous layer was extracted with dichloromethane, dried (MgSO4), filtered, and concentrated to afford crude product that was purified on PTLC (dichloromethane/methanol, 9:1) to provide pure 5-(3-fluoropropyl)-3-(2-(5)-pyrrolidinylmethoxy) pyridine (4 mg, 81%). NMR (p-toluenesulfonate salt in CD3OH, 500 MHz)-ppm: 8.27 (d, 1H, J=1.6 Hz), 8.19 (d, 1H, J=6.8 Hz), 7.68 (dd, 2H, J=6.5, 1.7 Hz), 7.63 (s, 1H), 7.22 (d, 2H, J=7.9 Hz), 4.46 (dt, 2H, J=47.4, 5.8 Hz), 4.38 (m, 2H), 4.08 (m, 1H), 3.40 (m, 2H), 2.84 (t, 2H, J=7.6 Hz), 2.36 (s, 3H), 2.3-1.9 (m, 6H). MS, m/z, 239 (100%, [M+H]$^+$).

5-(3-[[(4-Methylphenyl)Sulfonyl]Oxy]Propyl)-3-(1-BOC-2-(S)-Pyrrolidinylmethoxy)Pyridine The alcohol 8 (75 mg, 0.22 mmol) was dissolved in CH2Cl2 (1 mL) and treated with Et3N (100 μL) and p-toluenesulfonyl chloride (42 mg, 0.22 mmol). The reaction mixture was stirred at room temperature for 24 h. The mixture was washed with water (2×1 mL), dried (Na2SO4), and separated on PTLC (ethyl acetate/hexane, 1:1) to afford 10 (50 mg, 46%). NMR (CDCl$_3$, 500 Mz)-ppm: 8.10 (d, 1H, J=2.8 Hz), 8.0 (s, 1H), 7.94 (s, 1H), 7.78 (d, 2H, J=8.3 Hz), 7.22 (d, 2H, J=7.9 Hz), 4.21 (m, 1H), 4.11 (m, 2H), 4.05 (t, 2H, J=5.9 Hz), 3.60 (m, 2H), 2.72 (m, 2H), 2.47 (s, 3H), 1.99 (m, 6H), 1.55 (s, 9H). MS, m/z, 513 (100%, [M+Na]$^+$).

3-[2-(S)—N-tertbutoxycarbonyl-2-pyrrolinemethoxy]-2-Bromo-5-iodopyridine (Precursor for Niofene). To a solution of 2-bromo-5-iodopyridin-3-ol (Aldrich Chem. Co., 0.16 g, 0.55 mmol), N-Boc-L-3,4-dehydroproline was purchased from CNH Technologies, Inc., Woburn, Mass. (0.1 g; 0.50 mmol) and triphenylphosphine (0.19 g) in THF (10 mL), stirred under argon and cooled at 0° C., was added diisopropyl azodicarboxylate (DIAD; 0.2 mL). The reaction mixture was allowed to come up to ambient temperature over a period of 2 hrs and was stirred overnight. The reaction mixture was evaporated to dryness and the residue was purified by preparative TLC (1:4, EtOAc in hexane) to give pure product 3-[2-(S)—N-tertbutoxycarbonyl-2-pyrrolinemethoxy]-2-Bromo-5-iodopyridine as an oil. MS, m/z, 481, 483 (50%, [M+H]$^+$), 503, 505 (100%, [M+Na]$^+$).

3-[2-(S)—N-tertbutoxycarbonyl-2-pyrrolinemethoxy]-2-$^{18}$F-fluoro-5-iodopyridine ($^{18}$F-Niofene)

Synthesis of $^{18}$F-Niofene was carried out using our established procedures of $^{18}$F-nifene (Pichika et al., 2006). The automated radiosynthesis of $^{18}$F-Niofene was carried out in the automated unit. An Alltech C$_{18}$ column (10 μm, 250×10 mm$^2$) was used for reverse-phase HPLC purification and specific activity of $^{18}$F-Niofene was approximately 2000 Ci/mmol. The collected fraction was taken to near dryness in vacuo. The final formulation of $^{18}$F-Niofene was carried out using approx. 2 to 5 mL of saline (0.9% NaClINJ) followed by filtration through a membrane filter (0.22 μm) into a sterile dose vial for use in the PET studies.

3-[2-(S)-2-pyrrolinemethoxy]-5-iodopyridine (Niodene). 3-[2-(S)—N-tertbutoxycarbonyl-2-pyrrolinemethoxy]-5-iodopyridine Boron tribromide (BBr$_3$ 12 ml; 1M in CH$_2$Cl$_2$) was slowly added to a stirred solution of 3-Iodo-5-methoxypyridine (471 mg; 2 mmol) in CH$_2$Cl$_2$ (10 ml) at −40° C. (dry ice bath) and reaction mixture was left overnight stirring with gradual warming to ambient temperature. MeOH (7 ml) was slowly added and the reaction mixture was refluxed for 2 hrs. After removal of solvent, water was added and pH was adjusted to 7-8 by adding Na$_2$CO$_3$. The reaction mixture was extracted with EtOAc, dried over Na$_2$SO$_4$ and concentrated to yield crude product which was purified by prep-TLC using EtOAc/Hexanes (1:3) to furnish 3-Iodo-5-hydroxypyridine, (300 mg, 68%) as a solid compound. To a solution of (0.20 g, 1.0 mmol), 3-iodo-5-hydroxypyridine (0.24 g, 1.1 mmol) and triphenylphosphine (0.40 g, 1.5 mmol) in THF (10 mL), stirred under argon and cooled at 0° C., was added diisopropyl azodicarboxylate (DIAD; 0.3 mL, 1.5 mmol). The reaction mixture was allowed to come up to ambient temperature over a period of 2 hrs and was stirred overnight. The reaction mixture was evaporated to dryness and the residue was purified by preparative TLC (30% EtOAc in hexane) to give pure product (0.20 g, 50%) as an oil. $^1$H-NMR (500 MHz, CDCl$_3$) δ ppm: 8.41 (d, J=15.0, 1H, PyH), 8.25 (d, J=2.0, 1H, PyH), 7.56 (d, J=18.5, 1H, PyH), 5.88 (m, 2H, olefinic), 4.80 (m, 1H, C$\underline{H}$—CH$_2$), 4.34-3.95 (m, 4H, O—C$\underline{H}$, N—C$\underline{H}_2$), 1.48 (s, 9H, Boc). MS, m/z, 403 (100%, [M+H]$^+$). The BOC protected (90 mg; 0.22 mmol) in dichloromethane (5.0 mL) was treated with trifluoroacetic acid (TFA; 0.5 mL). The solution was stirred for 3 hrs at ambient temperature and concentrated to dryness at 50° C. Aqueous NaOH (10 mL, 1N) was added and the free base was extracted with dichloromethane (3×10 mL). The organic extract was dried over anhydrous MgSO$_4$, filtered and concentrated to yield as a free base (64 mg, 95%) and was found to be quite pure as per TLC, HPLC, NMR and Mass. MS, m/z, 303 (78%, [M+H]$^+$).

2-Fluoro-3-[2-{(S)—N-tert-butoxycarbonyl-3-pyrrolinyl}methoxy]-5-tributyltinpyridine (precursor for $^{123}$I-Niofene) and 5-tributyltin-3-[2-{(S)—N-tertbutoxycarbonyl-3-pyrrolinyl}methoxy]pyridine (precursor for $^{123}$I-Niodene)

To a solution of the respective bromo (approx. 20-30 mg) in anhydrous triethylamine (1 mL) under Argon, bistributyltin (100 mg; 0.17 mmol) and Tetrakis(triphenylphosphine)palladium(0) (5 mg) were added and the reaction mixture was refluxed overnight. Dark yellow crude reaction mixture was purified over prep silica gel TLC plate two times using 1/3: EtOAc/Hexanes as a solvent to yield the respective tributyl tin derivatives (5 to 10 mg) as an oil.

Radioiodination:

No-carrier-added Na$^{123}$I (MDS Nordion®, supplied in 0.1N NaOH) (5.0 mCi, approx 100 μL) was divided into four different vials. NaI (carrier) 25 μg, 10 μg, and 0 (no-carrier) was added in the 4 vials respectively. 1N HCl (20 μL), tributyltin precursors (500 μg dissolved in 200 μL EtOH), and chloramine-T trihydrate (50 μL of 1 mg/mL aq. stock) were added in sequence and the reaction mixture was incubated at room temp for about 2, 2.5, 3 and 4 hrs respectively. The reaction was quenched by adding NaHSO$_3$ (100 μL of 1 mg/mL aq. stock) and saturated NaHCO$_3$ solution (200 μL) was added. The reaction mixture was then extracted with CH$_2$Cl$_2$ (2×400 μL), dried (MgSO$_4$), evaporated (N$_2$ gas stream) and the crude $^{123}$I—N-Boc-derivatives were purified on HPLC (Econosil C18; 10 μm; 250×10 mm) using CH$_3$CN/H$_2$O (0.1% Et$_3$N): 60/40 at a flow rate of 2.5 mL/min and UV detector setting at 287 nm. The desired radioactive product was collected, evaporated to dryness and deprotected using 20% TFA in CH$_2$Cl$_2$ (1 mL) at 80° C. (external temperature of heating block) for 30 min. Solvents were subsequently evaporated to dryness, neutralized by NaHCO$_3$, formulated in saline and passed through 0.22 μm filter for biological experiments.

In further experiments, various compounds with a L-3,4-dehydroproline structure for imaging the alpha-4-beta-2 receptor subtype have been developed and evaluated (Pichika et al., 2005; J. Label. Compd. Radiopharm., 48: S9.). Such compounds included $^{18}$F-Nifrolene and $^{18}$F-Nifene. As can be seen from the experiments and data below, the advantage of the compounds in imaging studies is the faster binding kinetics due to rapid reversible binding, which resulted in shorter time duration of PET and SPECT studies.

In Vitro Binding Affinity

In vitro binding affinity of nifrolidine was measured in rat brain slices labeled with 125I-iodoepibatidine (125I-IEB) or 125I-α-bungarotoxin. The brains from male Sprague-Dawley rats (n=4 per group) were extracted and frozen in isopentane at 20° C.

Figure 3:
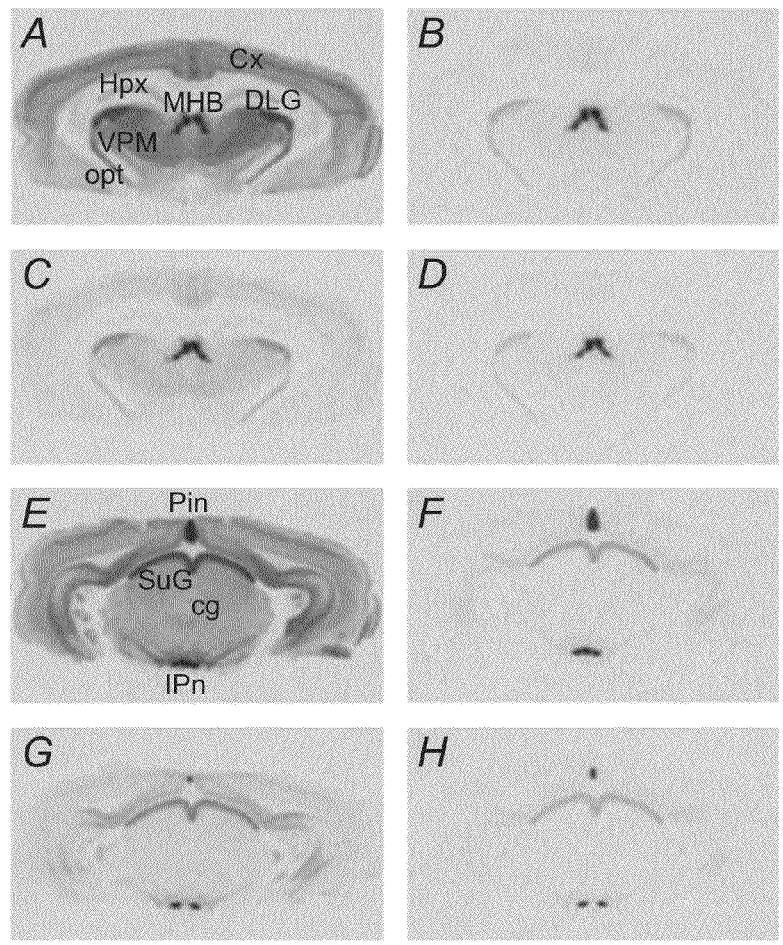
FIG. 3 depicts various radiographic images of inhibition of ¹²⁵I-IEB in rat brain slices by contemplated compounds (here: nifrolidine). (A) depicts binding of ¹²⁵I-IEB without nifrolidine and cytisine in cortex (Cx), hippocampus (Hpx), medial habenula (MHb), dorsolateral geniculate (DLG), ventral posteriomedial nucleus of thalamus (VPM), and optic tract (opt). (B) depicts binding of ¹²⁵I-IEB with 200 nmol/L cytisine. (C) depicts binding of ¹²⁵I-IEB in presence of 30 nmol/L nifrolidine. (D) depicts binding of ¹²⁵I-IEB in presence of 30 nmol/L nifrolidine and 200 nmol/L cytisine. (E) depicts binding of ¹²⁵I-IEB without nifrolidine and cytisine in pineal (Pin), superior colliculus (SuG), central gray (cg), and interpeduncular nucleus (IPn). (F) depicts binding of ¹²⁵I-IEB with 200 nmol/L cytisine. (G) depicts binding of ¹²⁵I-IEB in presence of 30 nmol/L nifrolidine. (H) depicts binding of ¹²⁵I-IEB in presence of 30 nmol/L nifrolidine and 200 nmol/L cytisine. (I) is a graph showing percent inhibition of ¹²⁵I-IEB by nifrolidine at α4β2, α3β2, and α3β4 receptor subtypes obtained from autoradiographic experiments.
Figure 3:
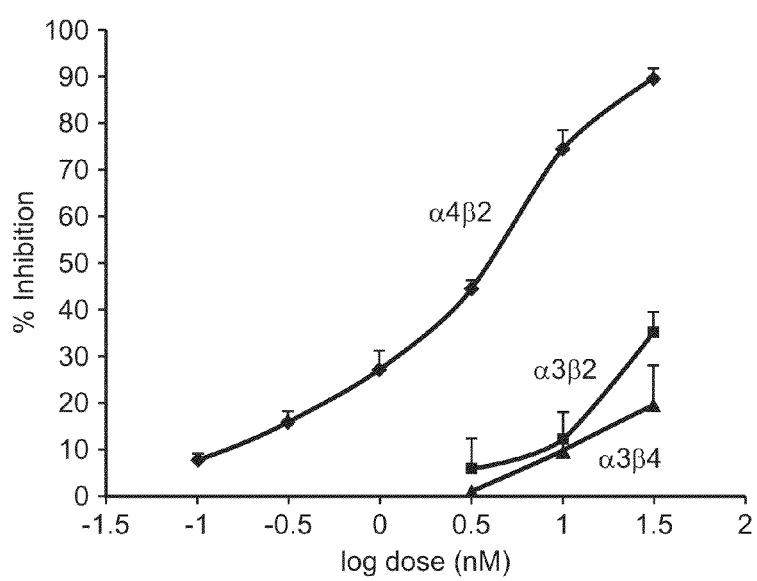

Coronal sections (20-μm thick) were prepared from 4 brain levels on a cryostat at 20° C. These levels included cerebellum (Bregma 11.3), superior colliculus (Bregma 6.0 to 6.42), and 2 thalamic areas (Bregma 4.3 to 3.8). For 125I-IEB studies, slides were preincubated at room temperature for 10 min in buffer (50 mmol/L Tris HCl, 120 mmol/L NaCl, 5 mmol/L KCl, 2.5 mmol/L CaCl2, 1 mmol/L MgCl2, pH 7.4) and then incubated with 0.08 nmol/L 125I-IEB at room temperature for 90 min. Competition studies were performed by incubating alternate sections with 125IIEB in the absence or presence of cytisine (200 nmol/L) and nicotine (300 μmol/L) and various concentrations of nifrolidine (0-30 nmol/L). Slides were then rinsed twice for 10 min in ice-cold buffer, dipped briefly in ice-cold water, blown dry, and laid out for autoradiography along with 125I plastic standards of known radioactivity (FIG. 3). For 125I-α-bungarotoxin binding competition studies, a similar method was used except that buffer consisted of 50 nmol/L Tris, pH 7.4, with 120 nmol/L NaCl. Slides were incubated at room temperature for 2 h with 125I-α-bungarotoxin (5 nmol/L) in the absence and presence of various concentrations of nifrolidine (0-30 nmol/L) and α-cobratoxin (10 mmol/L) to define nonspecific binding. Slides were apposed to Kodak Biomax MR films for 2 or 48 h and then developed and fixed.

Autoradiograms were quantified with a computer-based image analysis system (MCID; Imaging Research) using calibrated standards of reference. A calibration curve of to optical density against radioligand concentration (fmol/mg tissue) was constructed using values of known radioactivity. Optical densities in discrete regions of the autoradiographic images were measured, and corresponding values of radioactivity were determined by interpolation from the calibration curve. Specific binding values in each region were determined by subtracting binding in the presence of excess inhibitor from total binding values.

125I-IEB binding to heterogeneous sites can be discriminated by regional analysis of binding in the presence and absence of cytisine, which has modest selectivity for α4β2 nAChRs. Readings were obtained in various brain regions, including the pineal (Pin), interpeduncular nucleus (IP), medial habenula (MHb), optic tract (opt), superior colliculus (SuG), dorsolateral geniculate (DLG), central gray (CG), cortex (Ctx), and ventral posteriomedial nucleus of the thalamus (VPM). Specific binding to α4β2 sites was measured in the VPM, Ctx and CG, and was defined in the absence and presence of 200 nmol/L cytisine. Specific binding to a3 (32 sites was measured in the DLG, SuG and opt, and was defined as 125I-IEB binding in the presence of 200 nmol/L cytisine minus nonspecific binding in the presence of added nicotine (300 mmol/L). Specific binding to α3β4 sites was measured in the Pin, IP, and MHb and was defined as 125I-IEB binding in the presence of 200 nmol/L cytisine minus nonspecific binding in the presence of added nicotine (300 μmol/L). Specific binding of 125I-α-bungaratoxin to α7 nAChRs was measured in the ventrolateral geniculate (VLG) and the SuG and was defined as total binding minus nonspecific binding in the presence of α-cobratoxin (10 mmol/L). Concentration— response curves for nifrolidine inhibition of specific binding to each nAChR were constructed for each brain region. For a given nAChR type, inhibition values did not differ across brain regions. Complete inhibition curves were obtained only for α4β2 sites, and resulting inhibition constant (Ki) values were derived by nonlinear computerized regression using Prizm (GraphPad, San Diego).

Radiochemistry 5-(3-18F-Fluoropropyl)-3-(2-(S)-Pyrrolidinyl-methoxy)Pyridine(18F-Nifrolidine)

The radiosynthesis of $^{18}$F-nifrolidine was performed using an automated synthesis procedures that used a chemistry-processing computer unit (CPCU). $^{18}$F in $H_2{}^{18}O$ from the MC-17 cyclotron was passed through QMA-light Sep-Pak (Waters Corp.), preconditioned with 3 mL of K2CO3, 140 mg/mL, followed by 3 mL of anhydrous acetonitrile. The 18F trapped in QMA-light Sep-Pak was then eluted (using nitrogen gas) with 1 mL Kryptofix 2.2.2. (Merck)/K2CO3 (360 mg/75 mg in 1 mL of water and 24 mL of acetonitrile) and transferred to the CPCU reaction vessel. The SYNTH1 program in the CPCU was used for the synthesis that involved an initial drying step of the 18F-fluoride, Kryptofix 2.2.2., and K2CO3 mixture at 120° C. for 10 min. Subsequently, acetonitrile (2 mL) from CPCU reagent vial 2 was added and evaporated at 120° C. for 7 min to ensure dryness of this 18F-fluoride mixture.

Figure 4:
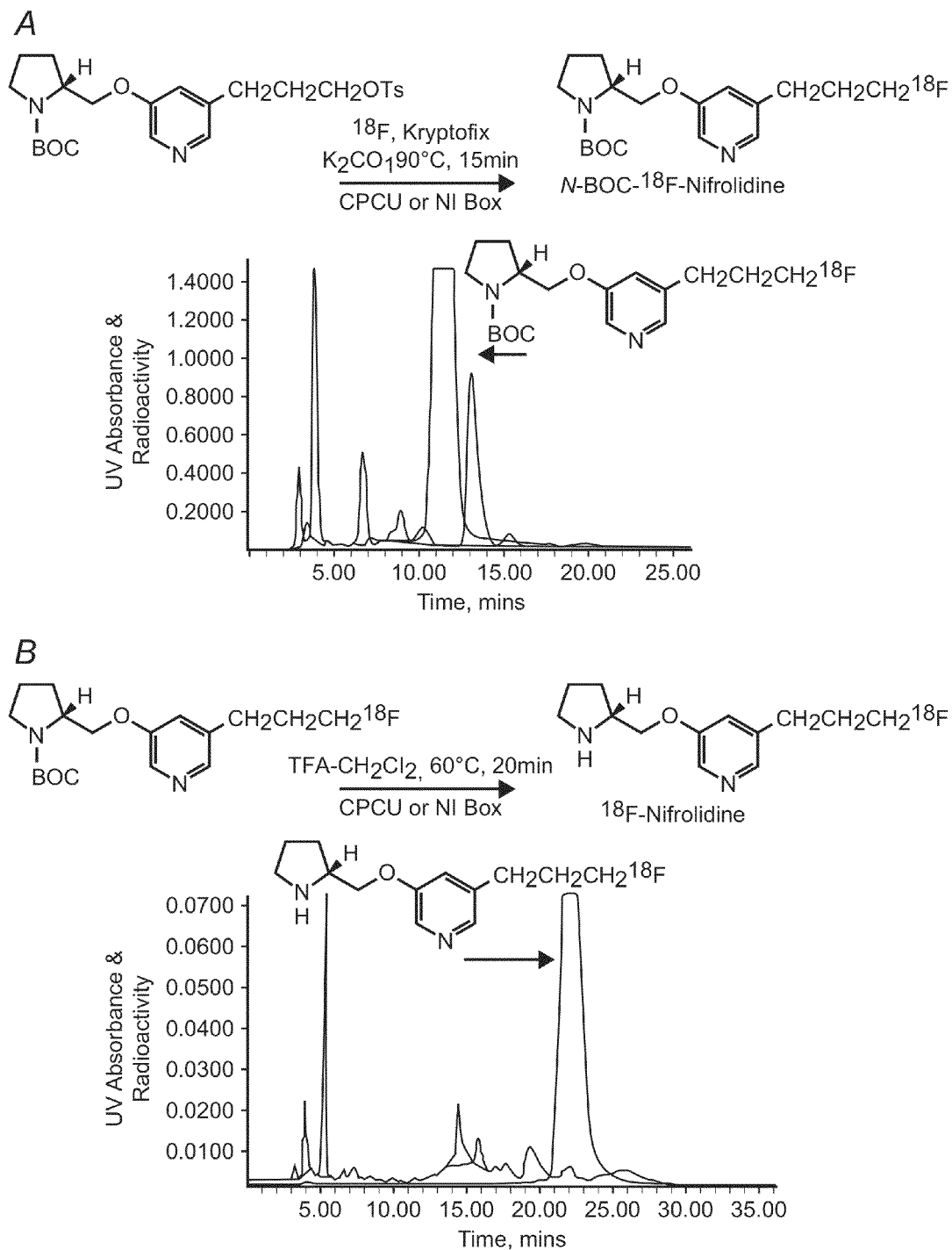
FIG. 4 (A) is an exemplary reaction scheme depicting radiosynthesis of ¹⁸FN—BOC-nifrolidine and HPLC purification of ¹⁸F—N—BOC-nifrolidine. (B) is an exemplary reaction scheme depicting radiosynthesis of ¹⁸F-nifrolidine and HPLC purification of ¹⁸F-nifrolidine.

After this, the precursor, 5-(3-[(4-methylphenyl)sulfonyloxy]propyl)-3-(1-BOC-2-(S)-pyrrolidinylmethoxy)pyridine 10 (3 mg in 1 mL of anhydrous acetonitrile contained in CPCU reagent vial 3) was added and the reaction proceeded for 15 min at 96° C. Subsequent to the reaction, $CH_2Cl_2$ (7 mL contained in CPCU reagent vial 4) was added to the mixture and the $CH_2Cl_2$ contents were passed through a neutral alumina Sep-Pak (prewashed with methanol) to remove any unreacted 18F-fluoride. The collected CH2Cl2 solution coming out of the CPCU now contained 5-(3-18F-fluoropropyl)-3-(1-BOC-2-(S)-pyrrolidinylmethoxy)pyridine. The CH2Cl2 was removed in vacuo and the residue was taken up for HPLC purification. The retention time of 5-(3-18F-fluoropropyl)-3-(1-BOC-2-(S)-pyrrolidinylmethoxy)pyridine was found to be 11-12 min using the solvent of 60% acetonitrile, 0.1 mol/L ammonium formate in water at a flow rate of 4.0 mL/min (FIG. 4A). The 5-(3-18F-fluoropropyl)-3-(1-BOC-2-(S)-pyrrolidinylmethoxy)pyridine fraction was collected into a flask and the solvent was removed in vacuo using a rotary evaporator. The residue was then dissolved in 1 mL CH2Cl2 and 0.2 mL of TFA. The solution was heated at 80° C. for 20 min. The residue was cooled at room temperature, solvents were removed in vacuo, and the residue was neutralized to pH 7 with 10% NaHCO3. This mixture was then purified with a gradient of 0.1 mol/L ammonium formate (100%)/acetonitrile (0%) at time 1 min to 0.1 mol/L ammonium formate (40%)/acetonitrile (60%) at time 35 min with a flow rate of 4.0 mL/min. The retention time of 5-(3-18F-fluoropropyl)-3-(2-(S)-pyrrolidinylmethoxy)pyridine (18F-nifrolidine) was found to be 21 min. The radiosynthesis was accomplished in 2.5 h from the end of bombardment with an overall radiochemical yield ranging 20%-40% decay corrected.

This collected fraction was taken to near dryness in vacuo. Approximately 5-8 mL of sterile saline (0.9% NaCl INJ [United States Pharmacopeia], 10-mL single dose; Abbott Laboratories) were added to the flask. The contents of the flask were then drawn into a 5- or 10-mL sterile syringe depending on volume. The contents of the syringe were then filtered through a 0.2-μm Millex-FG sterile filter (Millipore Corp.). This final dose was then used for in vitro and in vivo studies. The final dose of 18F-nifrolidine was used to determine specific activity using nifrolidine standards. An aliquot of 18F-nifrolidine was injected on a C18 analytic column (250×4.6 mm) and eluted with 0.1 mol/L ammonium formate (40%)/acetonitrile (60%) at a flow rate of 1.0 mL/min. The radioactivity peak of 18F-nifrolidine appeared at approximately 21 min. The mass peak corresponding to this peak was compared with nifrolidine standards. The specific activity of the 18F-nifrolidine was found to be 140±28 GBq/μmol (range, 111-185 GBq/μmol estimated in 10 radiosynthesis runs). To reduce total radiosynthesis time, only 1 HPLC purification for the 2-step radiolabeling reaction was investigated. After the first radiolabeling step, the product was extracted with CH2Cl2 as described and the solvent volume was reduced to approximately 1 mL by a stream of nitrogen gas. Into this reaction vial, TFA (0.2 mL) was added and then reacted as described. The residue was cooled at room temperature, solvents were removed in vacuo, and the residue was neutralized to pH 7 with 10% NaHCO3 and with a gradient of 0.1 mol/L ammonium formate (100%)/acetonitrile (0%) at time 1 min to 0.1 mol/L ammonium formate (40%)/acetonitrile (60%) at time 35 min with a flow rate of 4.0 mL/min. The retention time of 5-(3-18F-fluoropropyl)-3-(2-(S)-pyrrolidinylmethoxy)pyridine (18F-nifrolidine) was found to be 22 min (FIG. 4B). Because the specific activity of 1 HPLC separation was comparable with that observed with 2 HPLC separations, all subsequent radiosynthesis of 18F-nifrolidine used 1 HPLC purification.

In Vitro 18F-Nifrolidine Autoradiographic Studies

Coronal and horizontal brain slices (10- to 20-nm thick) were obtained from male Sprague-Dawley rats. Sets of brain slices were preincubated in buffer (50 mmol/L Tris HCl containing 120 mmol/L NaCl, 5 mmol/L KCl, 2.5 mmol/L CaCl2, 1 mmol/L MgCl2, pH 7.4) for 10 min (26). Subsequently, the slices were incubated with 18F-nifrolidine (37 kBq/mL in fresh buffer) at 25° C. for 60 min. Nonspecific binding was measured in the presence of 300 mmol/L nicotine (weighed as nicotine ditartarate). In some experiments, a lower concentration of nicotine (10 μmol/L) was also used. After incubation, slides were washed twice (1 min each) with ice-cold Tris HCl buffer, pH 7.4, followed by a quick rinse in cold deionized water. The slides were then air dried and apposed to phosphor screens overnight and read by the Cyclone Phosphor Imaging System (Packard Instruments Co). The amount of bound 18F-nifrolidine in the autoradiograms was evaluated in various brain regions (as digital light units [DLU]/mm2) using the Opti-Quant acquisition and analysis program (Packard Instruments Co).

In Vivo 18F-Nifrolidine Rodent Biodistribution Studies

Male Sprague-Dawley rats (200-250 g) were anesthetized with halothane and injected via tail vein with 18F-nifrolidine (approximately 3.7 MBq each; mass injected <0.01 ng of nifrolidine). The animals were allowed to recover from anesthesia and had free access to food and water. They were sacrificed at various times (5, 60, and 120 min after injection of 18F-nifrolidine) and the brains were excised. Thalamus, Ctx, cerebellum, and blood were isolated from each rat and placed in preweighed tubes and were counted for 18F radioactivity. Using a standard of the injectate and the weight of the isolated regions, the amount of 18F-nifrolidine was calculated as percentage dose per gram for each of the regions. In one group of rats, nicotine ditartarate, 10 mg/kg, was injected 5 min before administration of 18F-nifrolidine. Rats were sacrificed at 60 min after injection of 18F-nifrolidine and brain regions were evaluated as described.

Monkey PET Study

The male rhesus monkey (12 kg) was anesthetized using ketamine (10 mg/kg) and xylazine (0.5 mg/kg) and was subsequently maintained on 0.5%-1.5% isoflurane. Two intravenous catheters were placed, one on each arm, for purposes of administration of the radiopharmaceutical and for obtaining blood samples during the study. The head of the animal was placed in the gantry of an ECAT EXACT HR PET scanner and positioned in place with adhesive tape as described previously. A transmission scan using a 68Ge/68Ga rod source was acquired before administration of the radiopharmaceutical to correct for tissue attenuation of the coincident radiation. A dynamic sequence of scans for a total of approximately 150 min was acquired in the 3-dimensional mode immediately after administering approximately 148 MBq (mass injected, <0.3 μg of nifrolidine) of 18F-nifrolidine intravenously. Data in the final form are expressed in units of the percentage injected dose per milliliter (% ID/mL) or kilobecquerels per milliliter (kBq/mL). Areas showing maximal radioligand binding in the mediodorsal thalamus, ventrolateral thalamus, temporal Ctx, occipital Ctx, frontal Ctx, and cerebellum were delineated in the images. Time-activity curves were obtained for all these regions. To provide anatomic detail of the 18F-nifrolidine in the brain, the PET images were coregistered to an MR image of the rhesus brain. This MRI template of the rhesus (Macaca mulatta) brain is an average of 6 monkeys with T1-weighted MR scans. Postimage processing removed the skull and scalp from the template (courtesy of University of Wisconsin-Madison).

Results

Synthesis

The synthesis route to prepare nifrolidine 9 is shown in FIG. 2. Starting with 3,5-dibromopyridine 1,3-bromo-5-methoxypyridine 2 was prepared in approximately 60%-89% yield by treatment with sodium hydride in methanol. Using an alternate procedure of sodium methoxide in N,N-dimethylformamide, more reproducible results were obtained in this reaction. Demethylation of 2 with refluxing hydrogen bromide provided 3-bromo-5-pyridinol 3 in 82% yield. The mixture generally had to be refluxed for longer times than reported (36 h rather than 16 h) for the high yields. Protection of (S)-pyrrolidinemethanol 4 was performed with di-tert-butyldicarbonate to provide 1-BOC-2-(S)-pyrrolidinemethanol 5 in 88% yield (alternatively, 5 is also available from Aldrich Chemical Co.). Mitsonobu reaction coupling of 3 and 5 was performed by diethyl azodicarboxylate in the presence of triphenylphosphine to provide the bromopyridyl ether 6 in 44% yield, which is somewhat lower than reported. To introduce a 3'-propanolic group at the 5-position, an allyl group was introduced. Using reported procedures, allylation of this bromo derivative 6 was first performed by allyltributyl tin in the presence of catalytic amounts of tetrakis(triphenylphosphine)palladium to provide the 5-allylpyridyl ether derivative 7 in 57% yield. Hydroboration of the allyl group followed by alkaline hydrogen peroxide treatment using previously described conditions led to the important alcohol intermediate, 8 in 26% yield. The low yield in this step was probably a result of the formation of a BH3 complex of the alcohol 8. Some preliminary efforts to neutralize this BH3 complex were not successful. Similar BH3-complex formation has recently been reported for other amines. The substituted alcohol 8 was treated with DAST to convert the alcohol to the corresponding fluoride using methods that we have previously used. Removal of the N—BOC group was achieved by treating with TFA to provide 9 in 25% to yield. Final product 9, nifrolidine, was used as a p-toluenesulfonate salt for in vitro binding assays. For radiolabeling with 18F, the tosylate 10 was prepared from the BOC-protected key alcohol intermediate 8 by reacting with toluenesulfonyl chloride in yields of 40%-50%. The tosylate 10 was found to be stable and suitable for 18F radiolabeling and was stored at 0° C. to 20° C.

In Vitro Binding Affinity

Binding of 125'-IEB in rat brain slices followed a previously reported pattern. Specific binding to $\alpha4\beta2$ subtypes such as VPM, CG, and Ctx were defined in the absence and presence of cytisine (FIG. 3). Specific binding to $\alpha3\beta2$ subtypes was measured in DLG, SuG, and opt in the presence of cytosine, and specific binding to $\alpha3\beta4$ subtypes was identified in Pin, IP, and MHb in the presence of cytisine. As seen in FIG. 3C, nifrolidine at a concentration of 30 nmol/L was able to displace a significant amount of 125I-IEB bound at the $\alpha4\beta2$ subtypes. A significantly lower effect was observed on 125I-IEB bound to the $\alpha3\beta2$ and $\alpha3\beta4$ receptor subtypes (FIGS. 3C and 3G). The dose-response curve of nifrolidine on the binding of 125IIEB at the 3 different receptor sites is shown in FIG. 31. The binding affinity of nifrolidine, Ki=2.89 nmol/L, was measured for the $\alpha4\beta2$ sites, whereas weaker affinities (>30 nmol/L) were measured for the $\alpha3\beta2$ and $\alpha3\beta4$ sites. Affinities for a7 sites using 125I-$\alpha$-bungaratoxin in brain slices revealed no measureable displacement up to a concentration of 30 nmol/L (data not shown). These findings suggest that among the 4 nAChR receptor subtypes tested, nifrolidine is a relatively selective compound to study the $\alpha4\beta2$ receptor subtypes. Similarly, the selectivity and subnanomolar affinity of Niofene results from its structural features resembling Nifene and Niodene.

Radiosynthesis

Figure 5:
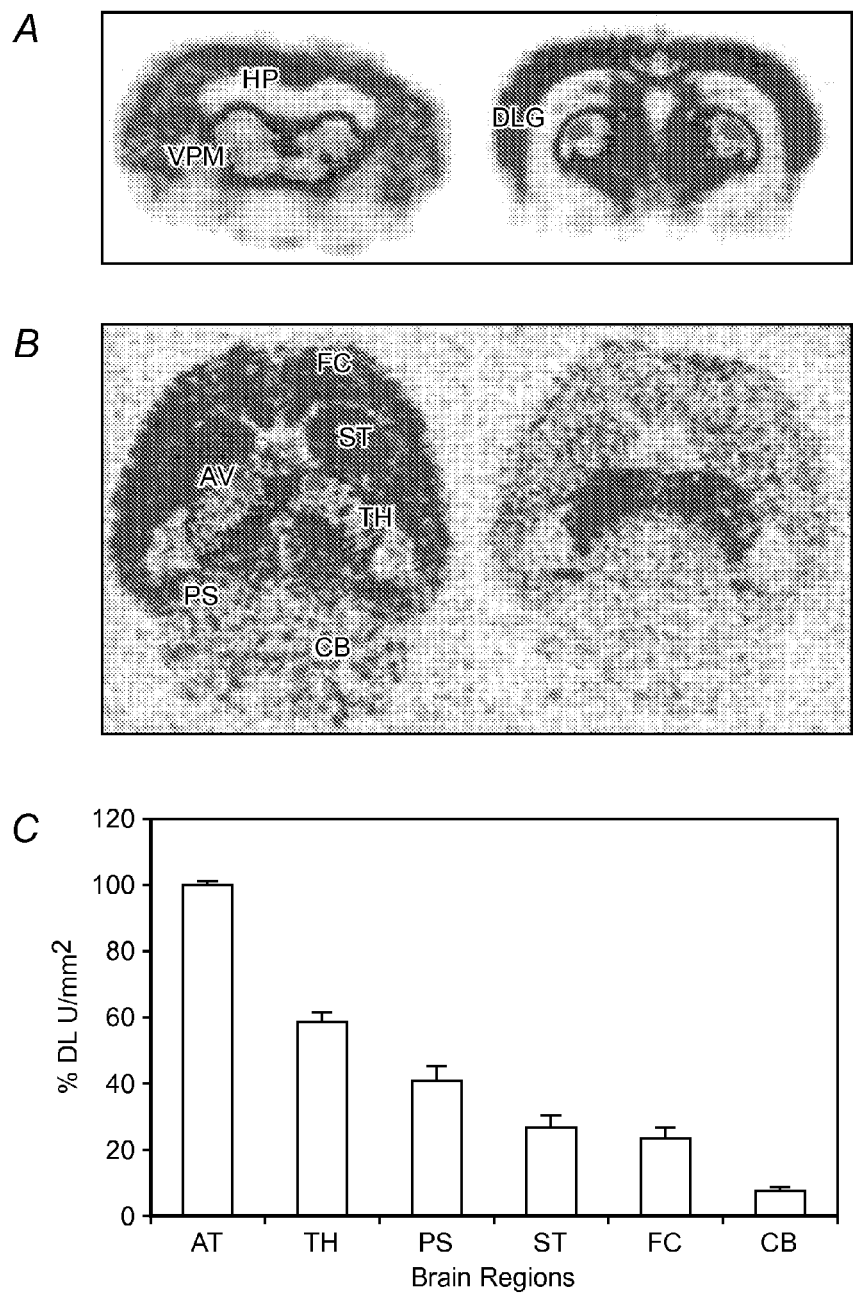
FIG. 5 shows results of in vitro autoradiographic studies of ¹⁸F-nifrolidine in rat brain slices. (A) illustrates binding of ¹⁸F-nifrolidine in 20-μm coronal slices (74 kBq/mL, 25° C.; HP=hippocampus). (B) illustrates total binding of ¹⁸F-nifrolidine in 10-μm horizontal slices (37 kBq/mL, 25° C.) and binding in presence of 10 μmol/L nicotine. FC=frontal cortex; ST=striata; AV=anteroventral thalamic nucleus; TH=thalamus; PS=postsubiculum; CB=cerebellum). (C) is a graph showing amounts of ¹⁸F-nifrolidine binding (DLU/mm²) in brain regions shown in FIG. 5B.

Radiosynthesis of 18F-nifrolidine required 2 steps. In the first step, 18F radiolabeling was performed by reacting the corresponding tosylate with 18F-fluoride (either from an MC-17 Scanditronix cyclotron or a RDS112 cyclotron) using Kryptofix 2.2.2. and K2CO3 in CH3CN at 100° C. for 15 min. This product was purified in reverse-phase HPLC as shown in FIG. 5. The radioactive peak was collected and the solvents were removed. The residue was dissolved in dichloromethane and used for the subsequent deprotection step. The purified radiolabeled BOC derivative was then deprotected (deprotection of the N—BOC-protecting group) with TFA at 80° C. for 25 min. This product mixture was again purified by HPLC. Radiosynthesis and 2 HPLC purifications took approximately 2.5 h and yielded the product in approximately 20%-40% decay-corrected radiochemical yield to provide 18F-nifrolidine in specific activities of 111-185 GBq/µmol. The high specific activity for nAChR ligands is essential because of the low concentration of these receptors in the brain and also because of the associated toxicity of these agents. To reduce total production time, only 1 HPLC purification was performed after the completion of the deprotection. The HPLC purification profile of this process is shown in FIG. 4B. Specific activities of 18F-nifrolidine were comparable with the 2-step purification and were produced in approximately 2 h in radiochemical yields of 20%-40%. Synthesis yields of SAKI were low, and may be due to steric effects of the bromine at the 2-position, adjacent to the hydroxyl group. Similarly 18F-Niofene (FIG. 11) was synthesized in high radiochemical yields using methods previously reported for $^{18}$F-Nifene (Pichika et al., 2006). Radiolabeling of $^{18}$F-Niofene was achieved successfully in >20% radiochemical yield in high specific activities >2 Ci/µmol.

In Vitro Autoradiographic Studies

As seen in FIG. 5A, in vitro autoradiography in coronal rat brain slices revealed selective binding of 18F-nifrolidine to thalamus, DLG, and other brain regions, such as the Ctx, known to contain $\alpha4\beta2$ sites. The hippocampus did not reveal any selective binding. Specific binding of 18F-nifrolidine was completely abolished by 300 mmol/L nicotine in these brain regions. In horizontal slices, binding of $^{18}$F nifrolidine was in the order thalamus>Ctx>striata>cerebellum, consistent with the known distribution of $\alpha4\beta2$ receptor sites. The anteroventral thalamic nucleus (AV) exhibited the highest amount of binding, as shown in FIGS. 5B and 5C, and is consistent with previous autoradiographic studies with $^{125}$I-IEB (26). Portions of the subiculum also exhibited significant amounts of 18F-nifrolidine binding, which is known to contain $\alpha4\beta2$ receptor sites (26). The cerebellum showed some binding (approximately 8% of that found in the AV). Nicotine at 10 mmol/L was able to partially displace the selective binding in various brain regions (FIG. 5B). These findings suggested the ability of 18F-nifrolidine to bind to $\alpha4\beta2$ receptor-rich regions.

In Vivo Rat Biodistribution Studies

Table 1 shows the binding in the various brain regions. Levels in the blood decreased from 0.25% ID/g at 2 min to <0.03% ID/g at 120 min. Binding in the thalamus was highest (>0.3% ID/g) at 60 min, after which time it exhibited significant clearance. The thalamus-to-cerebellum ratio was about 3 at 60 min. Binding in the Ctx was greater than that in the cerebellum. Ratios of the thalamus to the cerebellum decreased at 120 min, indicative of clearance of the radiotracer from receptor sites. Blocking studies were performed by subcutaneous injection of nicotine tartarate (10 mg/kg), which decreased binding in the thalamus (Table 1). These results suggest that 18F-nifrolidine is stable in vivo in rodents, is able to cross the blood-brain barrier, and is able to bind preferentially to $\alpha4\beta2$ receptor-rich regions, and the binding to receptor sites is reversible. Rats were preinjected subcutaneously with nicotine ditartarate (10 mg/kg) 5 min before injection of 3.7 MBq of 18F-nifrolidine. NT=not tested. Groups of male Sprague-Dawley rats (n=3) were injected intravenously with 3.7 MBq of 18F-nifrolidine and sacrificed at different times.

TABLE 1

| | BIODISTRIBUTION OF 18F-NIFROLIDINE IN RATS | | | | | |
|---|---|---|---|---|---|---|
| | % ID/g in various regions | | | | Thalamus-to-cerebellum ratio | |
| Time (min) | Blood | Thalamus | Cortex | Cerebellum | Control | Before nicotine* |
| 2 | 0.25 ± 0.09 | 0.26 ± 0.05 | 0.21 ± 0.04 | 0.24 ± 0.03 | 1.30 | NT |
| 60 | 0.14 ± 0.03 | 0.37 ± 0.07 | 0.25 ± 0.03 | 0.12 ± 0.02 | 3.08 | 1.8 |
| 120 | 0.04 ± 0.01 | 0.14 ± 0.03 | 0.13 ± 0.04 | 0.10 ± 0.02 | 1.40 | NT |

Autoradiography of $^{123}$I-niodene in rat brain sections revealed binding of $^{123}$I-niodene predominantly to the thalamus region of the brain which is the major target brain region for α4β2 receptors (FIG. 10). Binding of $^{123}$I-niodene was also observed in the cortex with the least amount of binding in the cerebellum. This is consistent with observations with $^{18}$F-nifene. With the use of low specific activity $^{123}$I-niodene, the binding ratio for thalamus to cerebellum was 4 while cortex to cerebellum ratio was 1.6. The thalamus to cerebellum ratio is lower for $^{123}$I-niodene compared to that observed for $^{18}$F-nifene, possibly due to the higher concentration of $^{123}$I-niodene (5 nM) compared to $^{18}$F-nifene (2.5 nM) in the incubation. The intensity of binding of $^{123}$I-niodene is weak due to the lower specific activity. Improvements in specific activity of $^{123}$I-niodene may provide higher target to cerebellum ratios of this potentially useful new SPECT imaging agent.

When radiolabeled with iodine-123, $^{123}$I-Niofene is expected to follow similar in vivo kinetics like $^{18}$F-Niofene and will thus have faster kinetics compared to the currently used SPECT agent, 5-IA. $^{18}$F-Niofene, an antagonist, has the potential to compliment our ongoing studies with $^{18}$F-Nifene, an agonist, for studies of α4β2 nAChRs in various animal models and human studies.

Monkey PET Studies

Figure 6:
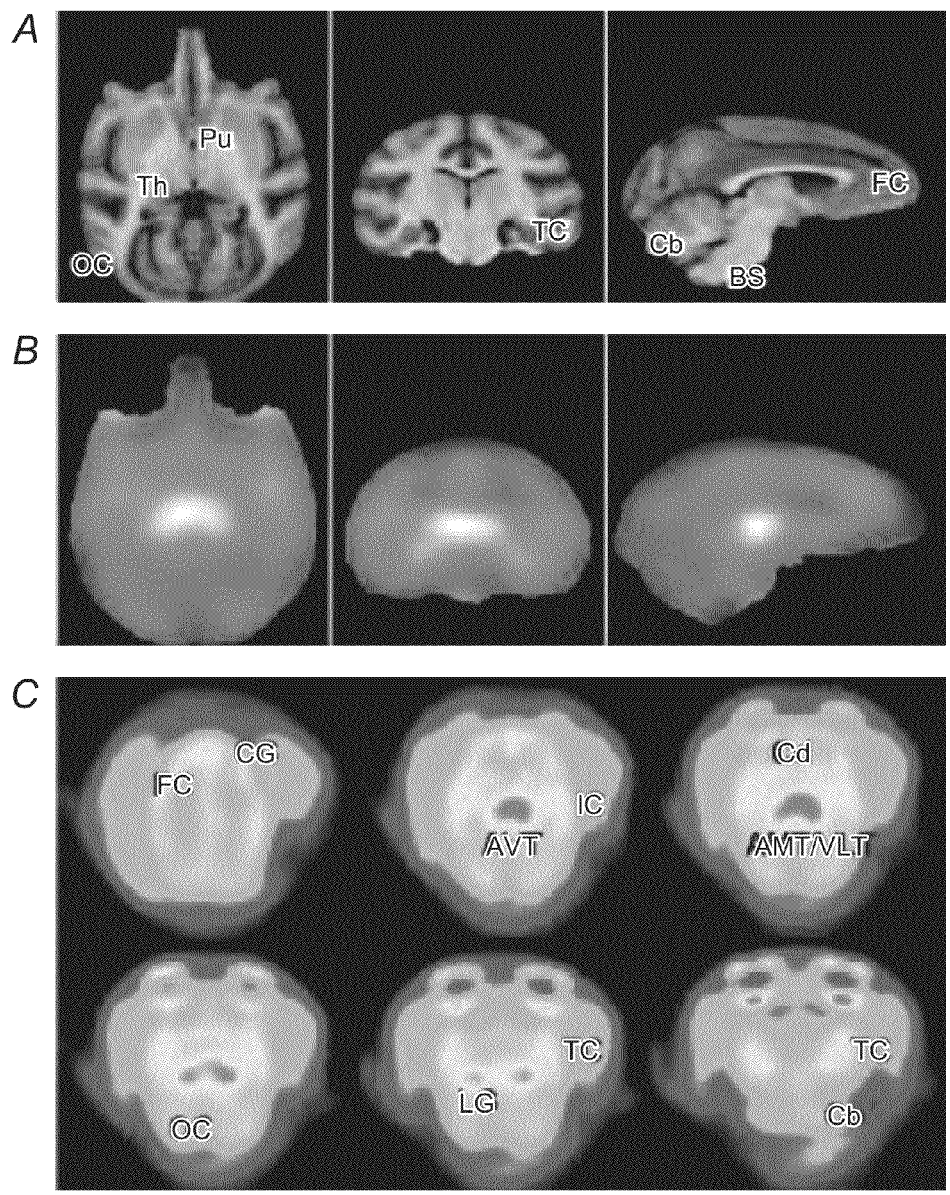
FIG. 6 depicts (A) MRI brain slice templates of rhesus monkey brain (axial, coronal, and sagittal sections) show putamen (Pu), thalamus (Th), occipital cortex (OC), temporal cortex (TC), frontal cortex (FC), cerebellum (Cb), and brain stem (BS). (B) Corresponding PET image slices acquired using ¹⁸F-nifrolidine. Images are shown in hot-metal color scale, where white indicates highest amount of radiotracer activity. (C) Depicts distribution of $^{18}$F-nifrolidine in rhesus monkey brain. Summed PET images (100-150 min) show binding of $^{18}$F-nifrolidine in select brain slices. Brain regions include cingulate gyms (CG), FC, anterioventral thalamus (AVT), insular cortex (IC), caudate (Cd), anteriomedial thalamus (AMT), ventrolateral thalamus (VLT), occipital cortex (OC), lateral geniculate (LG), temporal cortex (TC), and cerebellum (Cb).
Figure 7:
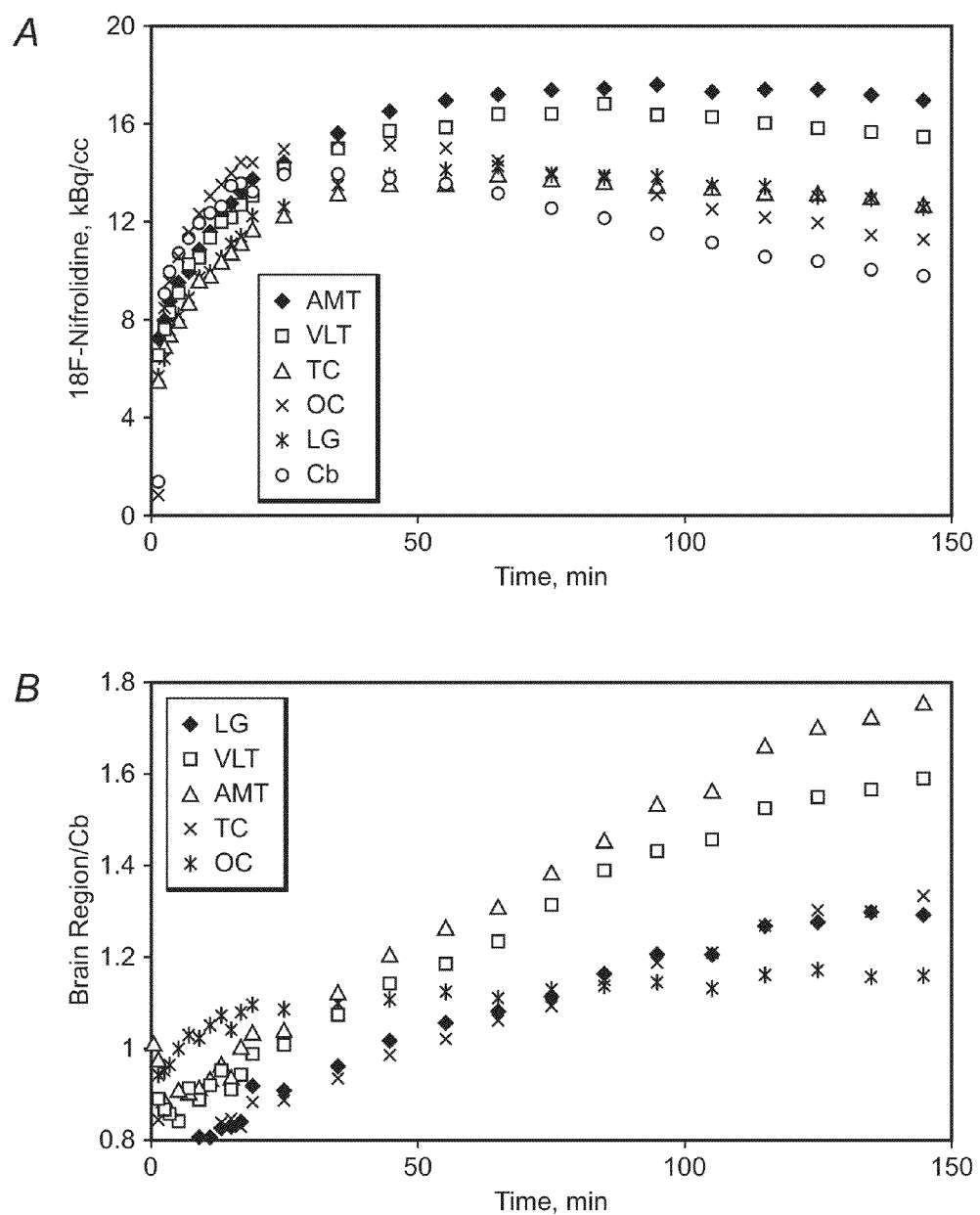
FIG. 7 depicts selected time-activity graphs in which (A) represents time-activity curves of $^{18}$F-nifrolidine binding in select areas of monkey brain corresponding to regions identified in FIG. 6C (AMT, VLT, TC, OC, LG, and Cb), and (B) represents a ratio plot of brain regions (in A) to Cb.

Given the promising results in rodents, we then performed a PET study of 18F-nifrolidine on an anesthetized rhesus monkey using an ECAT EXACT HR scanner. The monkey was administered 155 MBq of high-specific-activity (185 GBq/μmol) 18F-nifrolidine. Vital signs were closely monitored; the monkey did not exhibit any unusual deviations from the baseline values. Correlation with rhesus brain MRI templates (FIG. 6A) indicated a significant amount of binding in the thalamic regions seen in axial, coronal, and sagittal slices (FIG. 6B). The temporal Ctx and frontal Ctx had significant amounts of uptake, whereas the occipital Ctx exhibited lower binding. The cerebellum and brain stem had the least amount of uptake. A closer look at the axial slices is shown in FIG. 6C. The anteroventral thalamus (AVT), anteromedial thalamus (AMT), and ventrolateral thalamus (VLT) were regions that showed the highest uptake, which is consistent with the reported distribution of the α4β2 receptor subtype in the rhesus monkeys (31). Regions of moderate levels of binding included the lateral geniculate (LG; tentatively assigned) and cingulate gyms (CG), both of which are known to contain significant proportions of the α4β2 receptor subtype (31). Cortical regions such as insular Ctx (IC; tentatively assigned) and regions of the temporal Ctx (TC) showed relatively more binding than observed in other cortical regions. Some binding was also observed in other parts of the frontal Ctx (FC), occipital Ctx (OC), caudate (Cd), and cerebellum (Cb). Time-activity curves for the various brain regions are shown in FIG. 7A. Selective maximal uptake occurred in regions of the AVT and AMT (0.011% ID/mL), followed by the VLT (0.10% ID/mL). Significant selective binding was also seen in the FC and TC. Regions such as the striatum, for example, the caudate, showed little binding. The Cb showed a significant amount of uptake that slowly cleared during the course of the scan. The thalamus-to-Cb ratio approached a plateau of 1.7 in 120 min, whereas the cortical regions exhibited ratios of 1.3 in 120 min (FIG. 7B). These findings suggest that 18F-nifrolidine may be able to approach transient equilibrium somewhat sooner (about 2.5 hrs) than has been found with 2-18F-A85380 (22).

Figure 8:
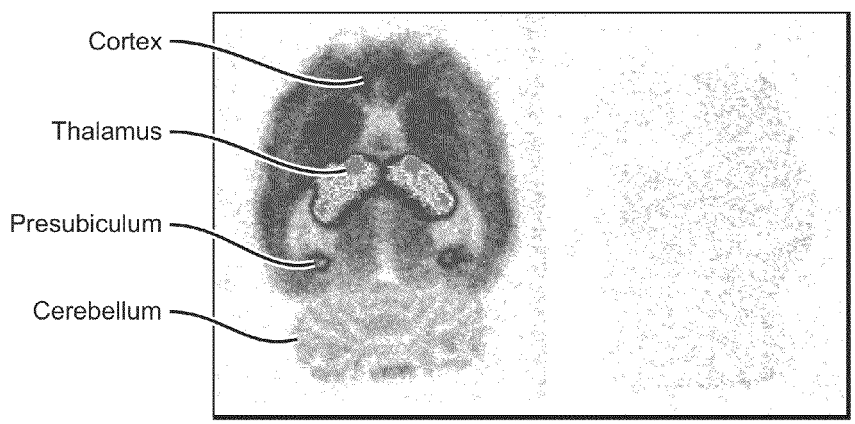
FIG. 8 depicts exemplary results from horizontal brain slices of rat brain showing binding of $^{18}$F-nifene to alpha4-beta2 receptors in the thalamus, presubiculum, and cortex in brain slice A which reflects the concentration of the receptors. Nicotine at a concentration of 60 μM was able to rapidly reverse the binding of $^{18}$F-nifene as seen in brain slice B.

FIG. 8 depicts exemplary results from horizontal brain slices of rat brain showing binding of $^{18}$F-nifene to alpha4-beta2 receptors in the thalamus, presubiculum, and cortex in brain slice A which reflects the concentration of the receptors. Nicotine at a concentration of 60 μM was able to rapidly reverse the binding of $^{18}$F-nifene as seen in brain slice B. Here, darker colors represent higher concentration of the receptors. Cerebellum does not contain significant amount of these receptors as evidenced by the above experiment.

In vivo PET in rats showed rapid uptake in the brain and selective localization in receptor regions such as the thalamus (TH). Results are shown in FIG. 10 for 18F-Niofene. Using cerebellum (CB) as the reference region pseudoequilibrium was achieved in 30-40 mins with TH/CB>2. Time to reach pseudoequilibrium was similar to $^{18}$F-Nifene (30-40 mins) and this time is considerably shorter when compared to 5-IA85380 and 2-FA85380 which is >4 to 6 hrs.

Discussion of Results

The initial design strategy for this series of compounds was to incorporate fluoroalkyl groups at the 5-position on the pyridine ring in the pyridylether compounds (FIG. 1D). The n-propyl and n-3'-fluoropropyl derivative maintain a high degree of structural similarity. Therefore, as a first derivative in our fluoroalkyl series, we developed the putative antagonist nifrolidine as a potential PET agent for this receptor. Radiolabeled 5-iodo-A85865 (Ki=1.2 nmol/L), which is structurally similar to nifrolidine (an iodine instead of the 3'-fluoropropyl group), has shown some selective retention in the thalamus in SPECT studies (23).

The synthesis of nifrolidine was accomplished using modifications of reported procedures for the synthesis of the pyridylethers. One of the unique aspects in contemplated compounds is the inclusion of the 5-(3'-fluoropropyl) group on the pyridine ring (FIG. 2). This required functionalization of the alkyl group both for introducing fluorine and for eventual radiolabeling with $^{18}$F. As in the case of dopamine D2 or D3 receptor agent fallypride, an allyl group was introduced at the 5-position to accomplish this task. The allyl group was converted to the corresponding alcohol. The alcohol thus served to introduce the fluorine or the $^{18}$F in the molecule. The yields of the various reaction steps were modest and are being currently optimized for the production of other derivatives. Nifrolidine was prepared as a p-toluenesulfonate salt for in vitro binding studies. Taking advantage of the binding of $^{125}$I-IEB to α4β2, α3β2, and α3β4 receptor subtypes, binding affinities of these sites for nifrolidine were determined autoradiographically as reported.

Nifrolidine exhibited high affinity (Ki=2.89 nmol/L) in the high affinity of 5-alkylated pyridylethers for this receptor subtype. Incorporation of the fluorine atom in the alkyl side chain did not have a detrimental effect on the binding of the compound. Weaker affinities (>30 nmol/L) were obtained for α3β2 and α3β4 receptor sites, thus demonstrating the good selectivity of nifrolidine for the α4β2 receptors. This is in contrast to the agonist A-85380, which has comparable affinities for α4β2 and α3β2 subtypes. Using 125I-bungaratoxin, affinities for α7 receptor sites were also found to be weak. Based on these initial binding studies, nifrolidine seems to have good selectivity for α4β2 sites over α3β2, α3β4, and α7 sites. In vitro binding affinities for other normicotinic receptor sites have yet to be performed.

The radiosynthesis of 18F-nifrolidine required a 2-step procedure because of a need to protect the pyrrolidine nitrogen using a BOC-protecting group. The N—BOC-protecting group has been used previously in the radiosynthesis of 18F-fluoro-A85380. The first step, nucleophilic displacement of the tosylate group, proceeded in high radiochemical yields and was typically done either in a computer-controlled CPCU box or in a nuclear interface box. This product was purified in high specific activities and was deprotected using TFA. A second chromatographic purification resulted in the final purified product 18F-nifrolidine with specific activities of 111-185 GBq/μmol. We have now also purified the product in a single HPLC purification with high specific activities (>111 GBq/μmol).

Specific activity is an important issue in imaging nAChRs. First, the receptors are in very small concentrations in the brain (1-6 fmol/mg in rat brains), which requires a high specific activity to avoid saturating the receptor sites. Second, there may be issues of toxicity with the nAChR imaging agents requiring radioligands with higher specific activities. Binding of 18F-nifrolidine in rat brain slices revealed a specificity toward brain regions rich in α4β2 receptor. FIGS. 5A and 5B shows maximal binding in the AV, followed by other regions of the thalamus, including dorsal geniculate. This is consistent with the distribution observed for the α4β2 receptor subtype. Although the hippocampus has little α4β2, regions of the subiculum exhibited significant binding. The FC and striata had significant amounts of binding. The Cb exhibited the lowest amount of binding (FIG. 5C). The Cb, generally used as a reference region in some studies, does contain α4β2 receptors. Thus, care must be taken to identify a reference region in these studies. For example, in rodents an area within the hippocampus known to contain the lowest concentration of α4β2 receptors can be considered as a reference region. This low binding in the hippocampus is evident in FIGS. 5A and 5B. Nicotine (300 μmol/L) was able to completely block binding of 18F-nifrolidine to the receptor sites, whereas lower amounts of nicotine (10 μmol/L) revealed some residual specific binding. These findings suggested the ability of 18F-nifrolidine to localize in regions of α4β2 receptors in vitro and is consistent with previously reported radioligands.

The brain distribution in rats revealed the ability of $^{18}$F-nifrolidine to penetrate the blood-brain barrier and localize selectively in brain regions such as the thalamus. The maximal thalamus-to-Cb ratio was found to be 3 in about 60 min after injection. Although this uptake ratio is low compared with that of other radiotracers, it does indicate that $^{18}$F-nifrolidine may be able to achieve a transient equilibrium in vivo in 2-3 h. The selectivity of binding to the thalamus (and reduction of the thalamus-to-Cb ratio on nicotine pretreatment) indicated promising in vivo characteristics. The imaging study in a rhesus monkey indicated good uptake of $^{18}$F-nifrolidine in the various regions of the brain. Coregistration with the MRI template confirmed localization of $^{18}$F-nifrolidine to the thalamus (FIGS. 6A and 6B). The thalamus exhibited the highest amount of binding, which is consistent with previous reports using other radioligands, such as 2-$^{18}$F-A85380 and $^{18}$F-epibatidine analogs. Binding was also seen in other parts of the brain, such as the TC and other cortical regions. The Cb and brain stem showed lower binding compared with that of the thalamus and Ctx. Several extrathalamic regions were identified in the serial axial slices. The CG, FC, areas in the TC, insular cortex, VLT, and LG were identifiable. These regions have not been identified previously with the agonist-based radiotracers. Time-activity curves in FIG. 7A reveal a plateauing effect in various regions, including the thalamus. Maximal binding in the thalamus occurs after 70 min following injection. Clearance from the Cb is slow; previous studies have shown a small amount of specific binding in the Cb to α4β2 receptors. In this study, the Cb was used as the reference region; other potential reference regions with lower α4β2 receptors in the monkey studies are being investigated because the Cb has been considered inadequate as a reference region. The ratio between the thalamus and the Cb was approximately 1.7 at about 140 min after injection (FIG. 7B). Thalamus-to-Cb ratios for the pyridylether PET radiotracers have ranged from 1.8 to 2.8 at 2 h after injection, whereas the epibatidine analogs have shown ratios of 2.9-4.2 at 2 h. Plateauing of the thalamus to-Cb ratio in 150 min in the case of 18F-nifrolidine may reflect faster kinetics. In vitro and in vivo studies are currently underway to further validate the in vivo kinetic parameters of 18F-nifrolidine and other structural analogs.

Figure 9:
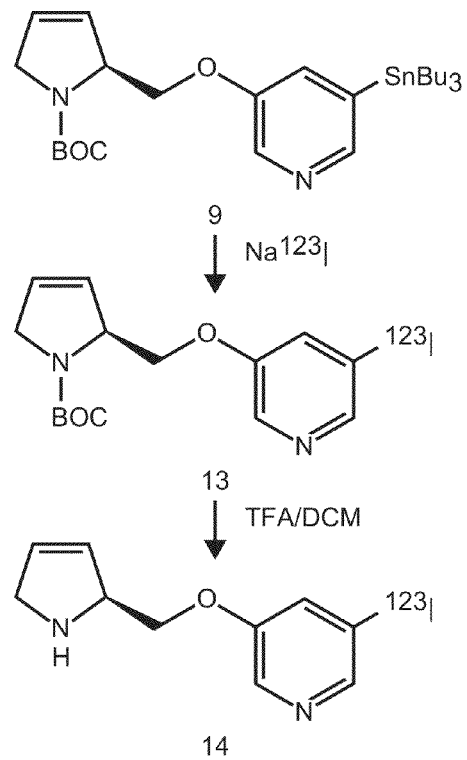
FIG. 9 shows A. Radiolabeling of $^{123}$I-niodene using sodium $^{123}$I-iodide in the presence of chloramine-T. B. HPLC purification of $^{123}$I—N—BOC-niodene of the reaction carried out in the presence of added 25 μg of sodium iodide. The UV peak corresponding to $^{123}$I—N—BOC-niodene is the unlabeled N—BOC-niodene.
Figure 9:
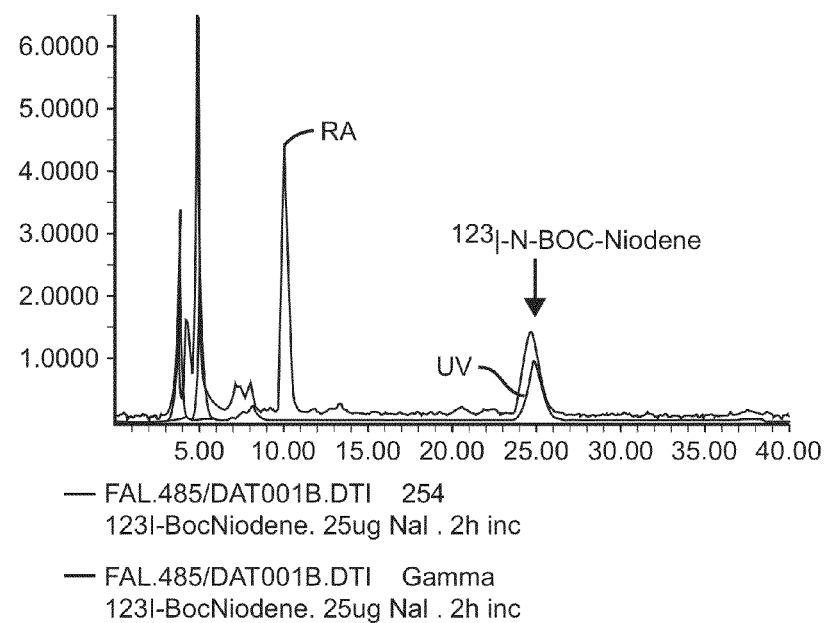

Presently, $^{123}$I-5-IA-85380 is used in human studies and requires over 6 hrs of scanning time, thus increases patient discomfort. We have designed and synthesized 3-iodo-5-[2-(5)-3-pyrrolinylmethoxy]pyridine (Niodene, FIG. 9)) with the aim to have faster binding kinetics compared to $^{123}$I-5-IA-85380, which may reduce scanning time and help in imaging studies. Binding affinity $K_i$ of niodene for rat brain α4β2 receptors in brain homogenate assays using $^3$H-cytisine was 0.27 nM. Niodene, 10 nM displaced >95% of $^{18}$F-nifene bound to α4β2 receptors in rat brain slices. By using the iododestannylation method, $^{123}$I-niodene was obtained in high radiochemical purity (>95%) but with low radiochemical yield (<5%) and low specific activity (~100 Ci/mmol). Autoradiograms show $^{123}$I-niodene localized in the thalamus and cortex, which was displaced by nicotine (thalamus to cerebellum ratio=4; cortex to cerebellum ratio=1.6). Methods of radioiodination need to be further evaluated in order to obtain $^{123}$I-niodene in higher radiochemical yields and higher specific activity of this potentially useful new SPECT imaging agent.

Figure 12:
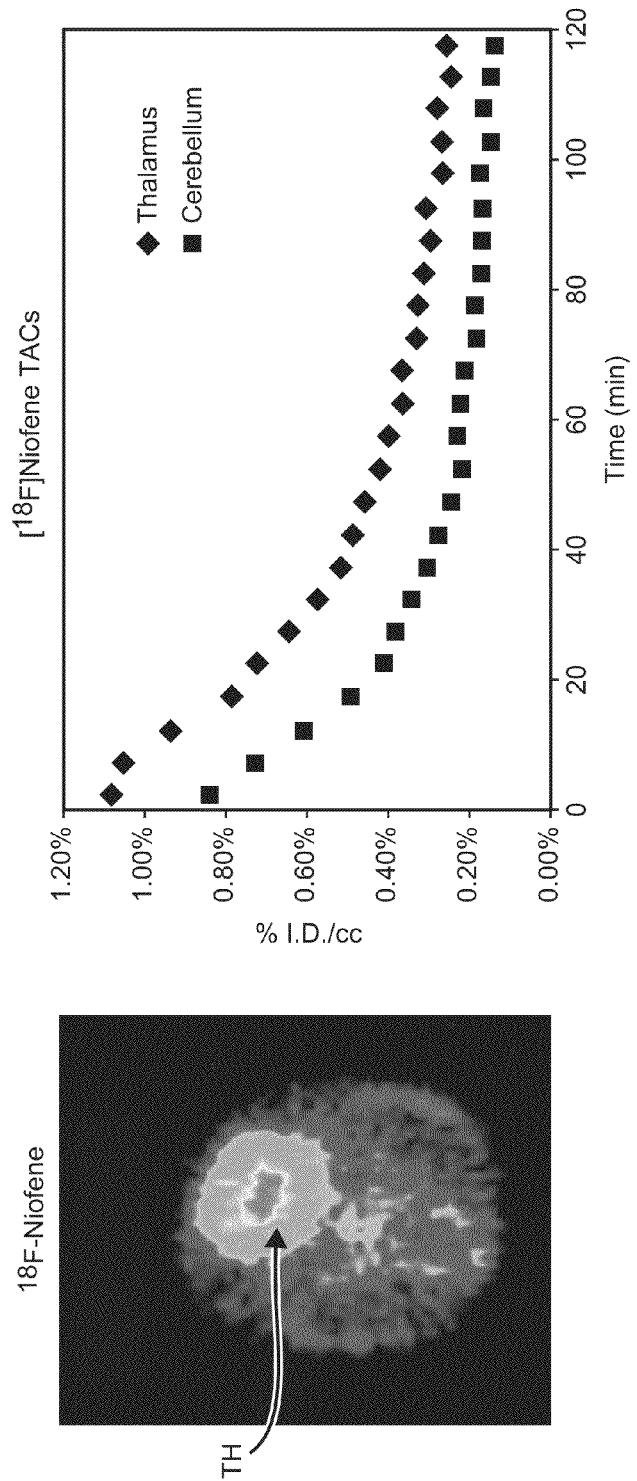
FIG. 12 shows a rat coronal brain slice showing thalamus (TH) with 18F-niofene binding on the left and on the right is shown the time-activity curve of 18F-niofene in thalamus and cerebellum

Novel PET/SPECT imaging agent $^{18}$F-Niofene was developed which shows rapid in vivo kinetics similar to that observed for $^{18}$F-Nifene. In vivo PET in rats showed rapid uptake in the brain and selective localization in receptor regions such as the thalamus (TH) (FIG. 12). Using cerebellum (CB) as the reference region, pseudoequilibrium was achieved in 30-40 mins with TH/CB>2. Time to reach pseudoequilibrium was similar to $^{18}$F-Nifene (30-40 mins) and this time is considerably shorter when compared to 2-FA, which is >4 to 6 hrs. When radiolabeled with iodine-123, $^{123}$I-Niofene is expected to follow similar in vivo kinetics like $^{18}$F-Niofene and will thus have faster kinetics compared to the currently used SPECT agent, 5-IA.

$^{18}$F-Niofene, an antagonist, has the potential to compliment our ongoing studies with $^{18}$F-Nifene, an agonist, for studies of α4β2 nAChRs in various animal models and human studies. In Alzheimer's disease (AD), α4β2 nAChRs may be affected due to the accumulation of Aβ-amyloid plaques (Aβ) and neurofibrillary tangles (NFT) in the hippocampus (HP) and frontal cortex (FC). $^{18}$F-Niofene is a potential diagnostic marker for PET studies of AD.

Thus, specific embodiments and applications of labeled alpha-4-beta-2 ligands and methods therefor have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

REFERENCES

Unless stated otherwise, all publications and patents are incorporated by reference herein. Where a definition or use of a term in a reference, which is incorporated by reference herein is inconsistent or contrary to the definition of that term provided herein, the definition of that term provided herein applies and the definition of that term in the reference does not apply.

Romanelli M N, Gualtieri F. Cholinergic nicotinic receptors: competitive ligands, allosteric modulators, and their potential applications. Med Res Rev. 2003; 23: 393-426.

Lukas R J. Diversity and patterns of regulation of nicotinic receptor subtypes. Ann NY Acad. Sci. 1995; 757:153-168.

Levin E D. Nicotine receptor subtypes and cognitive function. J. Neurobiol. 2002; 53:633-640.

Paterson D, Nordberg A. Neuronal nicotinic receptors in the human brain. Prog Neurobiol. 2000; 61:75-111.

Benowitz N L. Pharmacology of nicotine: addiction and therapeutics. Annu Rev Pharmacol Toxicol. 1996; 36:597-613.

Benwell M E, Balfour D J, Anderson J M. Evidence that tobacco smoking increases the density of [3H]nicotine binding sites in human brain. J. Neurochem. 1988; 50:1243-1247.

Nyback H, Halldin C, Ahlin A, Curral M, Eriksson L. PET studies of the uptake of S and R-11C-nicotine in the human brain: difficulties in visualizing specific receptor binding in vivo. Psychopharmacology. 1994; 115:31-36.

Badio B, Daly J W. Epibatidine, a potent analgetic and nicotinic agonist. Mol. Pharmacol. 1994; 45:563-569.

Sihver W, Nordberg A, Langstrom B, et al. Development of ligands for in vivo imaging of cerebral nicotinic receptors. Behav Brain Res. 2000; 113:143-157.

Brown L L, Pavlova O, Mukhin A, Kimes A S, Horti A G. Radiosynthesis of 5-(2-(4-pyridinyl)vinyl)-6-chloro-3-(1-[11C]methyl-2-(S)-pyrrolidinylmethoxy)-pyridine, a high affinity ligand for studying nicotinic acetylcholine receptors by positron emission tomography. Bioorg Med. Chem. 2001; 9:3055-3058.

Iida Y, Ogawa M, Ueda M, et al. Evaluation of 5-11C-methyl-A-85380 as an imaging agent as an imaging agent for PET investigations of brain nicotinic acetylcholine receptors. J Nucl Med. 2004; 45:878-884.

Roger G, Lagnel B, Rouden J, et al. Synthesis of a [2-pyridinyl-18F]-labelled fluoro derivative of (−)-cytisine as a candidate radioligand for brain nicotinic α4β2 receptor imaging with PET. Bioorg Med. Chem. 2003; 11:5333-5343.

Fujita M, Seibyl J P, Vaupel B, et al. Whole body distribution, radiation absorbed dose, and brain SPET imaging with 123I-5-I-A85380 in healthy human subjects. Eur J Nucl Med. 2002; 29:183-190.

Kimes A S, Horti A G, London E D, et al. 2-[18F]F-A-85380: PET imaging of brain nicotinic acetylcholine receptors and whole body distribution in humans. FASEB J. 2003; 17:1331-1333.

Bottlaender M, Valette H, Roumenov D, et al. Biodistribution and radiation dosimetry of 18F-fluoro-A-85380 in healthy volunteers. J Nucl Med. 2003; 44: 596-601.

Ding Y-S, Fowler J, Logan J, et al. 6-[18F]Fluoro-A-85380, a new PET tracer for the nicotinic acetylcholine receptor: studies in the human brain and in vivo demonstration of specific binding in the white matter. Synapse. 2004; 53:184-189.

Lena C, Changeaux J-P. Allosteric modulations of the nicotinic acetylcholine receptor. Trends Neurosci. 1993; 16:181-186.

Ochoa E L M, Chattopadhyay A, McNamee M G. Desensitization of the nicotinic acetylcholine receptor: molecular mechanisms and effect of modulators. Cell Mol. Neurobiol. 1989; 9:141-178.

Lin N H, Gunn D E, Li Y, et al. Synthesis and structure-activity relationships of pyridine modified analogs of 3-[2-((S)-pyrrolidinyl)methoxy]pyridine, A-84543: a potent nicotinic acetylcholine receptor agonist. Bioorg Med Chem. Lett. 1998; 8:249-254.

Lin N H, Li Y, He Y, et al. Synthesis and structure-activity relationships of 5-substituted pyridine analogs of 3-[2-((S)-pyrrolidinyl)methoxy]pyridine, A-84543: a potent nicotine receptor ligand. Bioorg Med Chem. Lett. 2001; 11: 631-633.

Abreo M A, Lin N H, Garvey D S, et al. Novel 3-pyridyl ethers with subnanomolar affinity for central neuronal nicotinic acetylcholine receptors. J Med. Chem. 1996; 39:817-825.

Chefer S I, London E D, Koren A O, et al. Graphical analysis of 2-[18F]FA binding to nicotinic acetylcholine receptors in rhesus monkey brain. Synapse. 2003; 48: 25-34.

Fan H, Scheffel U A, Rauseo P, et al. 125/123I-5-Iiodo-3-pyridyl ethers: synthesis and binding to neuronal nicotinic acetylcholine receptors. Nucl Med. Biol. 2001; 28:911-921.

Lin N-H, He Y, Holladay M W, Ryther K, Li Y, inventors; X, assignee. 3-Pyridyloxymethyl heterocyclic ether compounds useful in controlling chemical synaptic transmission. U.S. Pat. No. 5,629,325. Month, day, 1997.

Comins D L, Killpack D L. Lithiation of methoxypyridines directed by a-amino alkoxides. J Org. Chem. 1990; 55:69-73.

Perry D C, Xiao Y, Nguyen H N, Musachio J L, Davila-Garcia M I, Kellar K J. Measuring nicotinic receptors with characterisitics of α4β2, α3β2 and α3β4 subtypes in rat tissues by autoradiography. J. Neurochem. 2002; 82:468-481.

Ospina J A, Broide R S, Acevedo D, Robertson R T, Leslie F M. Calcium regulation of agonist binding to α7-type nicotinic acetylcholine receptors in adult and fetal rat hippocampus. J. Neurochem. 1998; 70:1061-1068.

Mukherjee J, Narayanan T K, Christian B T, Shi B, Dunigan K, Mantil J. In vitro and in vivo evaluation of the binding of the dopamine D2 receptor agonist 11C—(R,S)-5-hydroxy-2-(di-n-propylamino)tetralin in rodents and nonhuman primate. Synapse. 2000; 37:64-70.

Mukherjee J, Yang Z Y, Das M K, Brown T. Fluorinated benzamide neuroleptics-3: development of (S)—N-[(1-allyl-2-pyrrolidinyl)methyl]-5-(3-[F-18]fluoropropyl)-2,3-dimethoxybenzamide as an improved dopamine D-2 receptor tracer. Nucl Med. Biol. 1995; 22:283-296.

Shiue G G, Fang P, Shiue C Y. Synthesis of N,N-dimethyl-2-(2-amino-4-18F-fluorophenylthio)benzylamine as a serotonin transporter imaging agent. Appl Radiat Isot. 2003; 58:183-191.

Han Z Y, Zoli M, Cardona A, Bourgeois J P, Novere N L. Localization of 3Hnicotine, 3H-cytisine, 3H-epibatidine, and 125I-a-bungaratoxin binding sites in the brain of Macca mulatta. J Comp Neurol. 2003; 461:49-60.

Carroll F I, Lee J R., Navarro H A, et al. Synthesis, nicotinic acetylcholine receptor binding, and antinociceptive properties of 2-exo-2-(2',3'-disubstituted-5'-pyridinyl)-7-azabicyclo[2.2.1]heptanes: epibatidine analogues. J Med. Chem. 2002; 45:4755-4761.

Horti A G, Koren A O, Ravert H T, et al. Synthesis of a radiotracer for studying nicotinic acetylcholine receptors: 2-18F-fluoro-3-(2(S)-azetidinylmethoxy)pyridine (2-18FA85380). J Labelled Compds Radiopharm. 1998; 41:309-318.

Dolle F, Dolci L, Valette H, et al. Synthesis and nicotinic acetylcholine receptor in vivo binding properties of 2-fluoro-3-[2(S)-2-azetidinylmethoxy]pyridine: a new positron emission tomography ligand for nicotinic receptors. J Med. Chem. 1999; 42:2251-2259.

Dumont F., et al. Synthesis of [$^{18}$F]NicFP: a potential α4β2 nicotinic acetylcholine receptor radioligand for PET. J. Label Compd Radiopharm. 2003; 46:1261-1268.

Pichika, R., Easwaramoorthy, B., Collins, D., Christian, B. T., Shi, B., Narayanan, T. K., Potkin, S. G. and Mukherjee, J.: Nicotine α4β2 receptor imaging agents. Part II. Synthesis and biological evaluation of 2-[$^{18}$F]fluoro-3-[2-(S)-pyrrolinyl-3,4-dehydromethoxy]pyridine ($^{18}$F-Nifene) in rodents and imaging by PET in non-human primate. *Nucl. Med. Biol.,* 33: 295-304, 2006.

Pichika, R., Easwaramoorthy, B., Christian, B. T., Shi, B., Narayanan, T. K., Collins, D., and Mukherjee, J.: Nicotine α4β2 receptor imaging agents. Part III. Synthesis and evaluation of 18F-Nifzetidine in rodents and imaging by PET in non-human primate. *Nucl. Med. Biol.,* 38: 1183-1192, 2011.

Pandey, S. K., Pan, S., Kant, R., Pan, M. L., Kuruvilla, S. A. and Mukherjee, J.: Synthesis and evaluation of $^{123}$I-Niodene as potential imaging agent for nicotinic α4β2 receptors. *Bioorg. Med. Chem. Lett.,* 22: 7610-7614, 2012.

Pichika, R., Kuruvilla, S. A., Patel, N., Vu, K., Sinha, S., Easwaramoorthy, B., Shi, B., Narayanan, T. K., Christian, B. and Mukherjee, J.: Nicotine α4β2 receptor imaging agents. Part IV. Synthesis and evaluation of $^{18}$F-Nifrolene in rodents and non-human primate by PET imaging. *Nucl. Med. Biol.,* 40: 117-125, 2013.

What is claimed is:

1. A compound according to Formula X

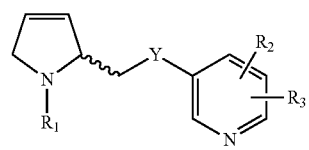

Formula X in which $R_1$ is hydrogen, a lower alkyl, or a nitrogen protecting group selected from the group consisting of a carbobenzyloxy group, a p-methoxybenzyl carbonyl group, a tert-butyloxycarbonyl group, a 9-fluorenylmethyloxycarbonyl group, an acetyl group, a trifluoroacetyl group, a benzoyl group, a benzyl group, a carbamate group, a p-methoxybenzyl group, a 3,4-dimethoxybenzyl group, a p-methoxyphenyl group, a tosyl group, and a nosyl group, Y is O, S, or $NR_1$, and $R_2$ and $R_3$ are independently a leaving group selected from the group consisting of a mesylate group, a tosylate group, a triflate group, a nosylate group, a nonaflate group, a brosylate group, a nitrate, a diazonium salt, a tetraalkylammonium salt, an ammonium salt, and a trialkyl tin group, or a halogen, or a halogen isotope.

2. The compound according to claim 1 wherein $R_2$ and $R_3$ are independently a halogen or a halogen isotope.

3. The compound according to claim 1 wherein $R_2$ and $R_3$ are both a halogen or both a halogen isotope.

4. The compound according to claim 1 wherein $R_2$ and $R_3$ are a halogen and a halogen isotope, respectively.

5. The compound according to claim 1 wherein $R_2$ is I and wherein $R_3$ is F, or wherein $R_2$ is $^{123}$I and wherein $R_3$ is F, or wherein $R_2$ is I and wherein $R_3$ is $^{18}$F.

6. The compound according to claim 1 wherein $R_2$ and $R_3$ are both a leaving group selected from the group consisting of a mesylate group, a tosylate group, a triflate group, a nosylate group, a nonaflate group, a brosylate group, a nitrate, a halogen, a diazonium salt, a tetraalkylammonium salt, an ammonium salt, and a trialkyl tin group.

7. The compound according to claim 1, having a structure according to Formula XI

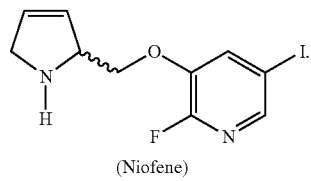

Formula XI (Niofene)

8. The compound according to claim 1, having a structure according to Formula XII

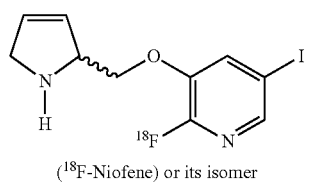

Formula XII ($^{18}$F-Niofene) or its isomer

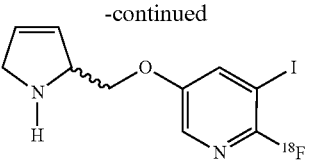

9. The compound according to claim 1, having a structure according to Formula XIII

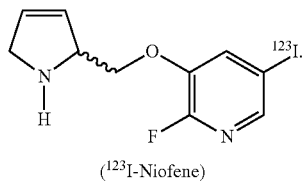

Formula XIII ($^{123}$I-Niofene)

10. The compound according to claim 1, having a structure according to Formula XIV

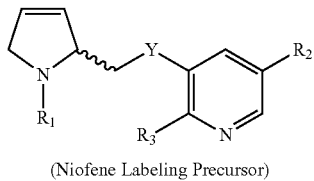

Formula XIV (Niofene Labeling Precursor)

in which $R_1$ is a nitrogen protecting group selected from the group consisting of a carbobenzyloxy group, a p-methoxybenzyl carbonyl group, a tert-butyloxycarbonyl group, a 9-fluorenylmethyloxycarbonyl group, an acetyl group, a trifluoroacteyl group, a benzoyl group, a benzyl group, a carbamate group, a p-methoxybenzyl group, a 3,4-dimethoxybenzyl group, a p-methoxyphenyl group, a tosyl group, and a nosyl group, or hydrogen, and in which $R_2$ and $R_3$ are independently a leaving group selected from the group consisting of a mesylate group, a tosylate group, a triflate group, a nosylate group, a nonaflate group, a brosylate group, a nitrate, a diazonium salt, a tetraalkylammonium salt, an ammonium salt, and a trialkyl tin group, or halogen.

11. The compound according to claim 1, having a structure according to Formula XIII

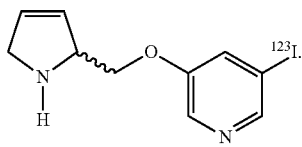

Formula XV ($^{123}$I-Niodene)

12. The compound according to claim 1, wherein the compound is 2-Fluoro-5-iodo-3-[2-(S)-3,4-dehydropyrrolinylmethoxy]pyridine (Niofene), or 2-$^{18}$F-5-iodo-3-[2-(S)-3,4-dehydropyrrolinylmethoxy]pyridine ($^{18}$F-Niofene), 2-Fluoro-5-$^{123}$I-iodo-3-[2-(S)-3,4-dehydropyrrolinylmethoxy]pyridine ($^{123}$I-Niofene), or 3-iodo-5-[2-(S)-3-pyrrolinylmethoxy]pyridine ($^{123}$I-Niodene).

* * * * *